US 6,597,969 B2

(12) United States Patent
Greenwald et al.

(10) Patent No.: US 6,597,969 B2
(45) Date of Patent: Jul. 22, 2003

(54) HOSPITAL DRUG DISTRIBUTION SYSTEM

(76) Inventors: Shlomo Greenwald, 113 Randolph Rd., Ithaca, NY (US); Zipora Greenwald, 113 Randolph Rd., Ithaca, NY (US)

( * ) Notice: Subject to any disclaimer, the term of this patent is extended or adjusted under 35 U.S.C. 154(b) by 2 days.

(21) Appl. No.: 09/888,995

(22) Filed: Jun. 22, 2001

(65) Prior Publication Data

US 2002/0198624 A1 Dec. 26, 2002

(51) Int. Cl.[7] .................................................. G06F 7/00
(52) U.S. Cl. ...................... 700/216; 700/225; 700/227; 700/230; 700/235; 700/242; 198/867.15
(58) Field of Search ............................ 700/216, 225, 700/226, 227, 228, 230, 231, 233, 235, 241, 242; 198/867.14, 867.15

(56) References Cited

U.S. PATENT DOCUMENTS

| | | | |
|---|---|---|---|
| 2,577,344 A | | 12/1951 | Masure ........................ 312/47 |
| 4,021,992 A | * | 5/1977 | Spaude et al. ................. 53/399 |
| 4,655,026 A | * | 4/1987 | Wigoda ........................ 53/55 |
| 4,778,045 A | * | 10/1988 | Grune et al. ........... 198/867.12 |
| 5,348,061 A | * | 9/1994 | Riley et al. .................. 141/104 |
| 5,533,606 A | * | 7/1996 | Yuyama ....................... 198/349 |
| 5,604,692 A | * | 2/1997 | Yuyama ....................... 708/714 |
| 5,660,305 A | * | 8/1997 | Lasher et al. ................. 221/206 |
| 5,771,657 A | * | 6/1998 | Lasher et al. ................... 53/55 |
| 5,812,410 A | * | 9/1998 | Lion et al. ................... 700/231 |
| 5,907,493 A | | 5/1999 | Boyer et al. ........... 364/479.01 |
| 5,915,524 A | * | 6/1999 | Horlacher ................ 198/473.1 |
| 5,963,453 A | * | 10/1999 | East ............................ 700/244 |
| 5,988,858 A | * | 11/1999 | Yuyama et al. ............. 700/230 |
| 6,181,979 B1 | * | 1/2001 | Murakami ................... 700/216 |
| 6,181,982 B1 | * | 1/2001 | Yuyama et al. ............. 700/236 |
| 6,219,587 B1 | * | 4/2001 | Ahlin et al. ................. 700/233 |
| 6,317,648 B1 | * | 11/2001 | Sleep et al. ................. 700/216 |

* cited by examiner

Primary Examiner—Khoi H. Tran
(74) Attorney, Agent, or Firm—Brown & Michaels, PC

(57) ABSTRACT

A hospital drug distribution system for efficiently distributing solid medicinal units to hundreds of patients comprises subsystems for placing trays on a conveyor, placing cups thereon, labeling the cups, conveying the cups under drug tubes, sealing the cups, unloading the trays, and coordinating the overall activities of the system. Medicinal units are stored in long, thin vertical tubes positioned side-by-side, and are dispensed by valves disposed at the bottom of each tube. The rows of tubes are suspended over a conveying means transporting individual medication cups. The cups are arranged on trays on the conveying means in single file. The computer-controlled conveying means proceeds in a step-and-stop fashion, such that each cup stops briefly beneath each drug tube. When a cup completes its journey beneath the drug tubes, it contains the drugs needed by the patient to which it is assigned. Barcode readers at each valve scan the approaching cup to determine if drugs from the attached tube should be dispensed into it. The system is modular, as additional modules including multiple tubes can be added or removed as needed. When a tube becomes empty, it is discarded or sent to a drug refilling center for restocking. The hospital orders from the refilling center all needed tubes daily, preferably automatically over a computer network by a computer that tracks drug inventory levels. Replacement tubes are delivered overnight or within hours, depending upon the need. The system preferably operates in manual mode for special one-time orders.

24 Claims, 12 Drawing Sheets

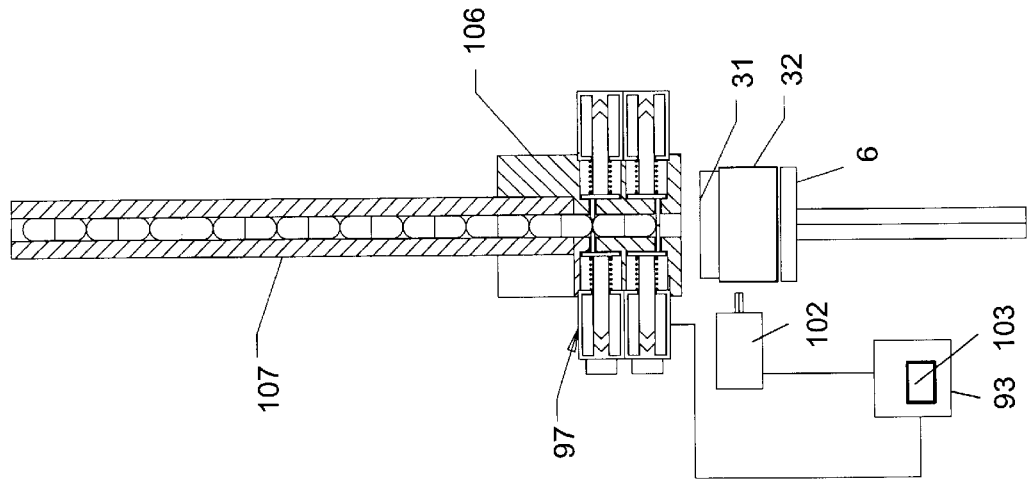
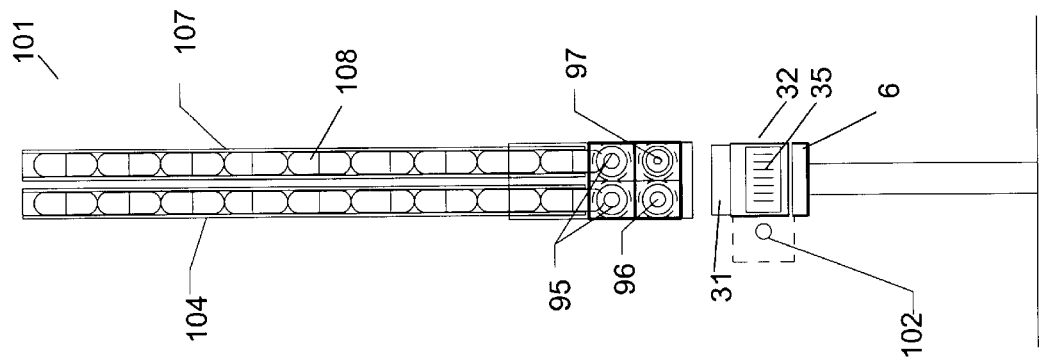
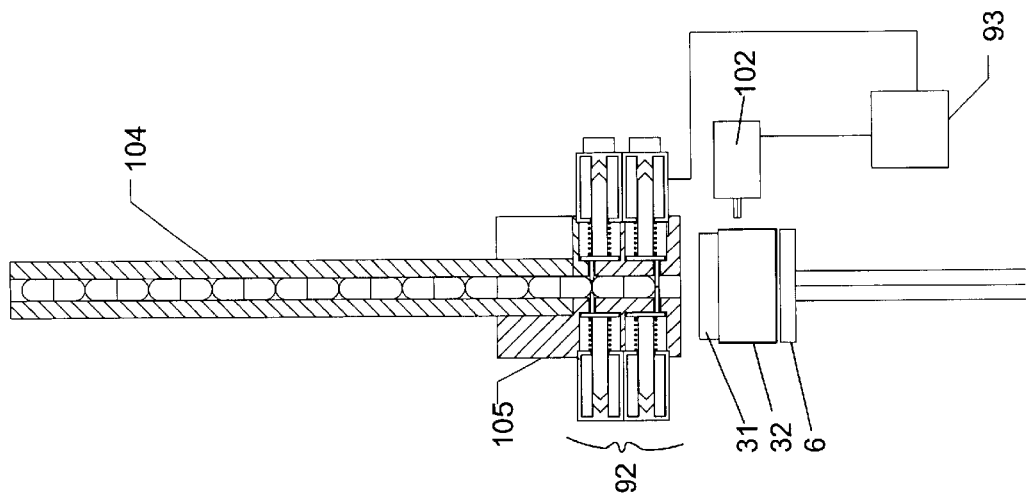

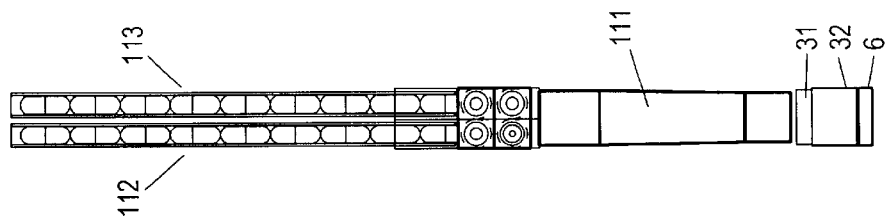
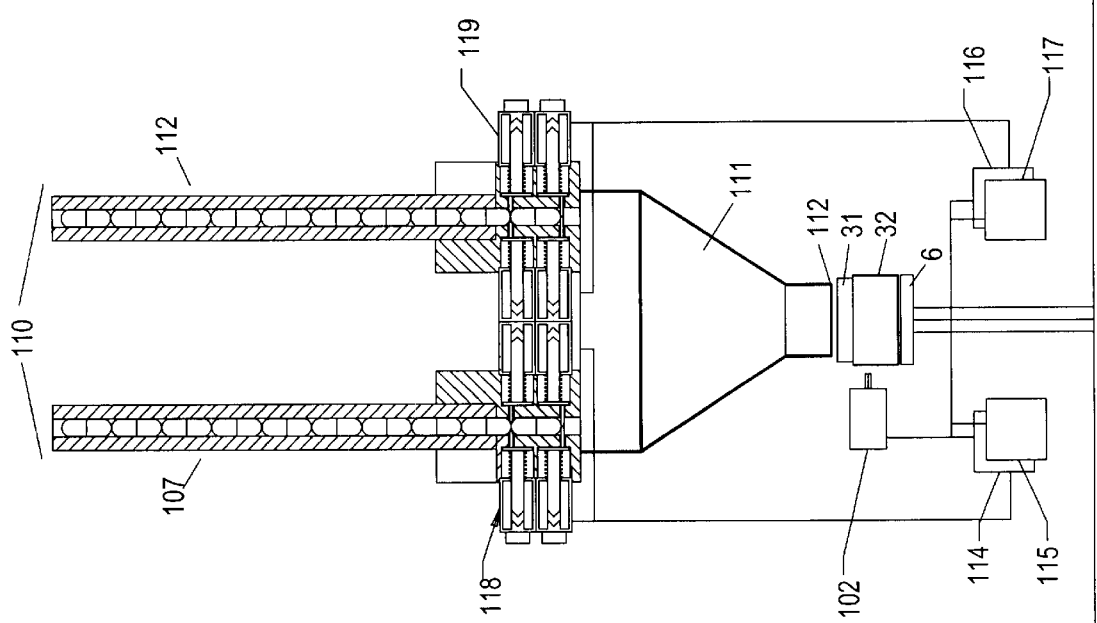
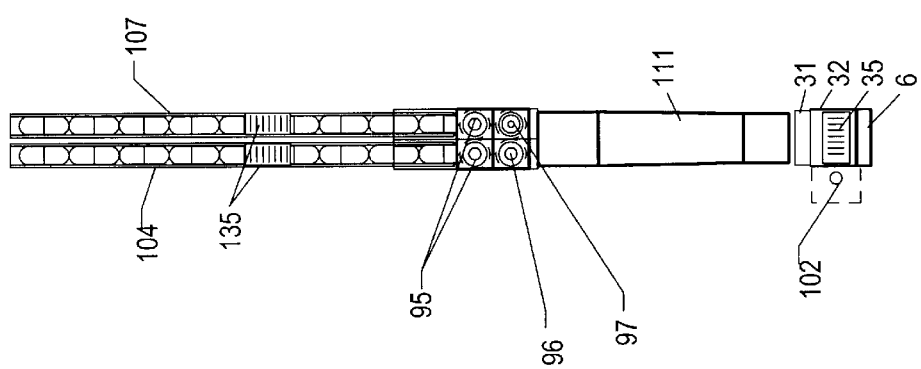

HOSPITAL DRUG DISTRIBUTION SYSTEM

BACKGROUND OF THE INVENTION

1. Field of the Invention

The invention pertains to the field of medication distribution systems. More particularly, the invention pertains to an efficient system for automatically dispensing and distributing solid medicinal units, such as pills and capsules, to patients, primarily in a hospital setting.

2. Description of Related Art

Various drug storage and dispensing devices are disclosed in the art. These devices are primarily concerned with efficient storage and dispensing of a number of pills or capsules based upon patient needs. There are few if any devices, however, directed to implementing a comprehensive, efficient, and error free means of distributing a few medicinal units to hundreds or thousands of patients simultaneously—such as in a hospital setting—where patients have varying medicinal needs that must be fulfilled at selected times of the day.

The invention disclosed in U.S. Pat. No. 2,577,344 is directed to a "Narcotic Dispenser" in which the drugs are stored in individual tubes, with a weight pressing them down, and the tubes are refilled and distributed to the dispenser. The tubes are kept side-by-side in a cabinet in which are visible all stored narcotic vials, and the number of units remaining for each. The invention contemplates use of a single cup which is manually positioned underneath the tube containing the particular narcotic to be dispensed. The apparatus does not, however, include means of automatically and simultaneously filling many cups with the medications needed by a large number of patients.

U.S. Pat. No. 5,907,493 is a "Pharmaceutical Dispensing System", for organizing a pharmacy by "sequentially and interactively" instructing pharmacists in filling prescriptions. The system uses a number of dispensers, each with a microprocessor. Barcode labels are printed and applied to vials. The vials are scanned, and a "ready to fill" light is lit on the dispenser. A microswitch detects the vial is in position, and the pills are dispensed. There is no conveyor system, and no provision to operate the system automatically for a number of vials—each vial must be separately, consecutively, and manually scanned, carried to the dispenser, filled, and capped.

Due to the above-described and other limitations, it is desirable to provide a medicament-dispensing system that compactly stores hundreds or thousands of different drugs, and dispenses the drugs accurately and efficiently for hundreds of patients, primarily in a hospital setting, at selected times of the day. Such a hospital drug distribution system should minimize the possibility of human error resulting in the wrong medication being dispensed. It should also be operable in a manual mode for exceptional cases where drugs are needed at other than the selected times of the day, or where only a small number of drug orders must be filled. Such might be the case, for example, in a small nursing home. Additionally, as the number of drugs to be handled by the system grows, the system should be able to grow accordingly in an efficient and cost-effective manner. For that reason, the system should be modular, to allow for easy expansion to include an ever larger set of drugs.

SUMMARY OF THE INVENTION

This application discloses and claims an invention that is useful in conjunction with an apparatus of the type shown and described in a commonly owned U.S. application entitled, "DRUG STORAGE AND DISPENSING APPARATUS," filed on the same day as the present application. That application is hereby incorporated by reference herein in its entirety.

The invention comprises a hospital drug distribution system, or HDDS, for dispensing and distributing solid medicinal units, such as pills, capsules, or the like (hereinafter, "medicinal units," or simply, "units"), automatically and efficiently, based upon patient needs. In the invented device, the medicinal units are stored in long, thin tubes, positioned vertically, side-by-side. Each tube has a valve at the bottom, with control electronics to dispense a precise number of units from the tube. The tubes are arranged, preferably, in a U-shaped arrangement, and are suspended over a conveying means which transports cups that receive the dispensed units. In the preferred embodiment, the conveying means transports the cups via cup-holding trays placed upon it, and there are nine to twelve cups per tray.

Prior to entering upon the conveying means, a cup-labeling subsystem draws data from the main computer database containing records of patients' medicinal needs. Based upon such data, this labeling subsystem places labels on cups on the conveying means, on the way to be filled with medicaments. Each label contains barcode-encoded data including the patient's name, location, and medicinal requirements. The label is placed by this subsystem on the side of a cup specially designed for receiving dispensed medicaments from the drug tubes. The cups are placed upon special trays and the trays conveyed upon the conveying means under each drug tube in turn, as described below.

The conveying means proceeds in a step-and-stop fashion, whereby each cup stops briefly beneath each drug tube. The progress of the cups through the system is controlled by a computer. If the cup underneath a particular drug tube pair is assigned to a patient who needs medicinal units stored in those tubes, the valve at the bottom of the active tube of the pair dispenses the required number of units into the cup. At each step, after all such dispensing has finished, the computer signals the conveying means to "step-and-stop" once again, thus moving each cup to the next tube pair. The cups are arranged on the conveying means in single file such that, during any given 'stop' period, there is only one cup underneath each tube pair. In such manner, each cup begins its journey at the beginning of the conveying means, and stops underneath each tube pair for possible dispensing of medicinal units. Because multiple cups make their way upon the conveying means simultaneously (and in single-file), dispensing of drugs is efficient as it takes place for multiple patients in parallel. The process begins with the first cup stopping under the first tube pair. In the next step, the first cup stops under the second tube pair, and the second cup stops under the first tube pair, and so on. When the cups reach the end of the conveying means, a tray-removal subsystem removes the trays therefrom and places them on special carts for distribution to the patients.

In one embodiment of the invented system, there is only one such cup per patient; by the time each cup has completed its journey and stopped briefly beneath each tube pair, it contains the exact mix, or "cocktail," of drugs needed by the patient to which it is assigned. In another embodiment, each cup holds only one type of medication, and hence, each patient has one or multiple cups. All cups assigned to a patient are delivered to the patient by a hospital staff member. The advantage of this one-cup-per-patient-per-medication embodiment is that, if any drugs go unused and the cups remain sealed, such unused drugs are returned to the drug refilling center for recycling into a new drug tube.

Each tube is stocked to contain a large number of units of the same medication. A valve at the bottom of each tube is specially designed for efficient dispensing of the appropriate number of medicinal units into the cup underneath it, according to data delivered to the valve's control electronics. For each set of valves there is a barcode scanner and reader (collectively, the barcode reader), disposed adjacent to the conveying means near the valves. The barcode reader scans and reads the barcode on the cup as the cup arrives underneath the valves to which the reader is coupled. The decoder interprets the barcode and transmits the code(s) of the required drug(s) to the valves. If any such code corresponds to the code of the drug dispensed by the valve, and if the valve is in "active" status, the valve dispenses the indicated number of medicinal units into the cup below. In this manner, at the end of the cup's journey upon the conveying means, it contains the number of units of the correct drug according to its barcode label.

The system is compact in that the drug tubes are thin. The system is also modular, in that additional modules containing, say, 100 tubes, can be added or removed as needed. The system is built by adding as many modules as are needed to accommodate the number of tubes necessary to serve the patients' medicinal needs. The tubes are preferably stored in pairs, such that there is a "primary" tube and a "backup" tube for each drug in the system. When one tube runs out, the other tube is activated and becomes the primary dispensing tube. Thus, the two tubes—the primary and the backup—have a means to communicate with each other so that, when the primary becomes empty (or malfunctions), the backup takes over dispensing medicinal units. In such event, the primary tube must be replaced; this is communicated to the Control computer of the invented system.

When any given tube becomes empty, it is either discarded or sent to a drug refilling center for re-stocking, depending upon the comparative costs of tube recycling versus purchasing of new tubes. The hospital, preferably daily, orders from such center all tubes (whether recycled or purchased new) that it presently needs or anticipates needing by the following day. Such tubes are preferably ordered automatically via a computer network by a control computer, which tracks drug inventory levels within the tubes of the HDDS. The replacement tubes are preferably delivered overnight or within hours, depending upon the need, to the hospital for installation into the HDDS.

BRIEF DESCRIPTION OF THE DRAWING

FIG. 10a shows a side view from the left of a valve unit (VU).

FIG. 10b shows a front view of a valve unit (VU).

FIG. 10c shows a side view from the right of a valve unit (VU).

FIG. 11a shows a front view of the front row of valve-units from FIG. 11b

FIG. 11b shows a cut-away view of two valve-units (VUs) mounted back-to-back.

FIG. 11c shows a front view of the back row of valve units from FIG. 11b.

DETAILED DESCRIPTION OF THE INVENTION

1. Introduction

Figure 1:
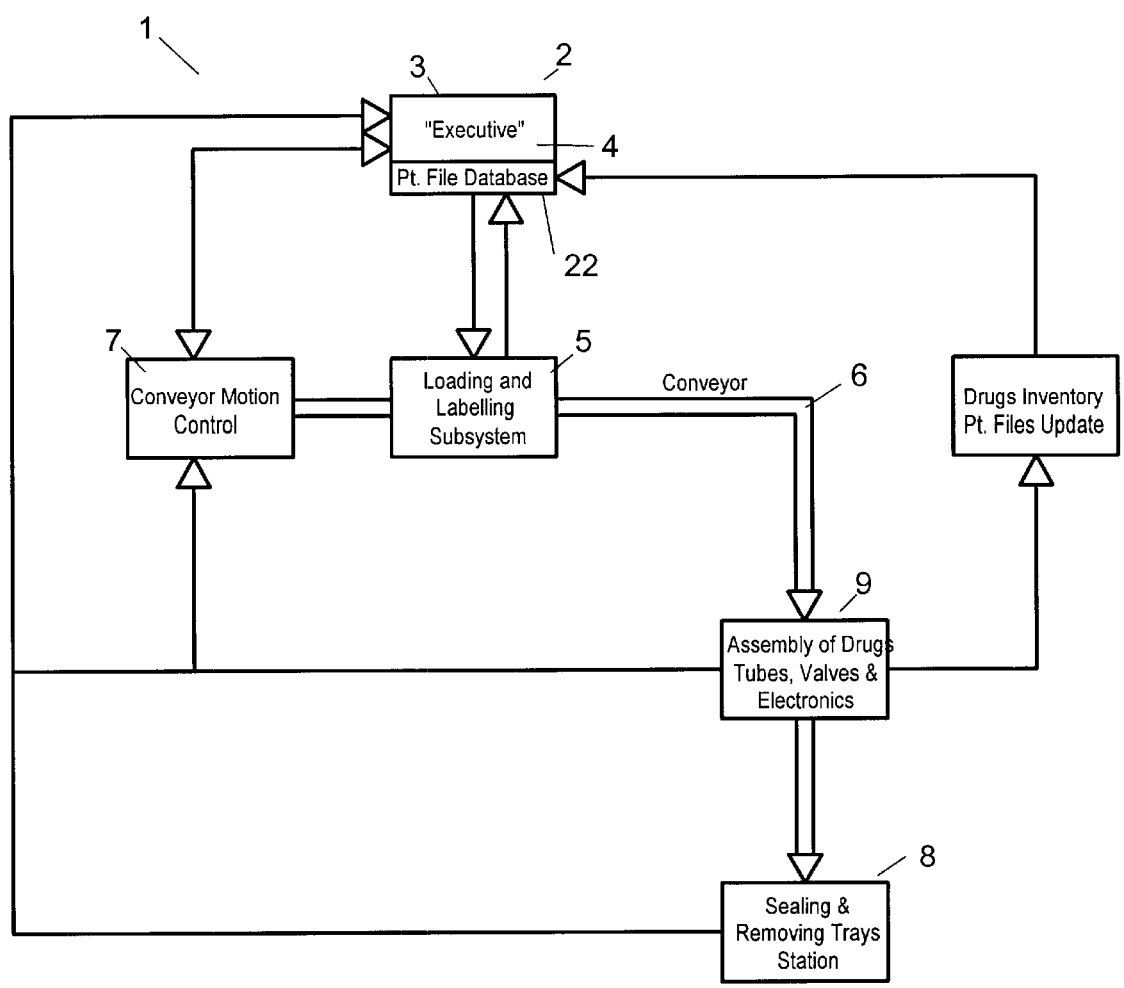
FIG. 1 is a block diagram of the invented hospital drug distribution system (HDDS).

To assist in a better understanding of the invention, a specific embodiment of the present invention will now be described in detail. Although such is the preferred embodiment, it is to be understood that the invention can take other embodiments. This detailed description will include reference to FIGS. 1 through 11. The same reference numerals will be used to indicate the same parts and locations in all the figures unless otherwise indicated. It will be apparent to one skilled in the art that the present invention may be practiced without some of the specific details described herein. In other instances, well-known structures and devices are shown in block diagram form.

The building blocks of the invented HDDS are the drug tubes and valves, where the drug tubes are tall, thin tubes containing medicaments, which tubes are ordered and reordered from a drug refilling center, and where there is disposed at the bottom of each tube a valve for dispensing the drugs from inside the tube. The valves have control electronics that, based upon information received from a barcode reader, determine how many units to dispense from the tube into a cup below. In one embodiment, the valve is permanently connected to the drug tube, in which case it is an integrated tube-valve, or ITV. In this embodiment, when the tube runs out of drugs, it is replaced by another ITV containing the same medication, and the empty ITV is returned to the drug refilling center. In another embodiment, the tube disconnects from the valve. The latter solution is particularly advantageous where empty tubes are discarded rather than returned to the drug refilling center for refilling, as it would be wasteful to discard the attached valve every time a tube becomes empty. In any event, the following assumptions are made: the tubes can be ordered and reordered from the drug refilling center via computer network, or by fax machine, or by any similar means of quick reordering; the valves include control electronics capable of receiving a signal to discharge a certain number of medicinal units from the tube to which it is coupled; upon receipt of such signal, the valve discharges the required number of medicinal units; the tubes are thin so that many can be stacked vertically side by side in a relatively small amount of space.

In the invented system the outside dimension of each tube and valve are the same as that of every other tube and valve, and the control electronics for each integrated tube/valve mechanism are the same as well. As noted, the tubes are tall and narrow, so that they hold many medicinal units, yet hundreds of tubes may be stacked side-by-side in a short distance. The tubes are arranged in modules of, preferably, 100 tubes per module, together with valves and control electronics. The HDDS is built by adding as many modules as needed for dispensing of most or all medications required by the hospital's patients. The HDDS meets the requirements of: reliability in dispensing the correct drugs to each patient; quickness of operation; ease and cost-effectiveness of maintenance; operability in automatic mode or manual mode.

2. The Hospital Drug Distribution System (HDDS)

Referring to FIG. 1, the HDDS (1) comprises five subsystems:

i) The Controlling subsystem (2): A main Control Computer (3) where the files of all the patients and the medications they need are updated daily running tracking and controlling software (4). This software, known as the "Executive," also tracks drug inventory, keeps an up-to-date status of each tube (i.e., the drug information, and quantity remaining), and reports to the operator when a tube is empty or otherwise needs to be replaced.

ii) The Loading/Labeling subsystem (5): A computerized subsystem that loads trays onto a Conveyor (6); places medication cups on the trays; and places on the side of each cup a label with patient information and barcode-encoded indicia of the medication code and quantity needed for that patient.

iii) The Conveying subsystem (7): A preferably U-shaped Conveyor (6) carrying trays loaded with medication cups. Preferably, the conveyor is an indexer-driven chain type conveying device, but it could be any other conveyor means without departing from the scope of the invention.

iv) The Sealing/Removing subsystem (8): A subsystem which places a seal on each cup after medication has been dispensed into it. When all cups on a particular tray have been sealed, this subsystem also places a cover over the tray, removes the tray from the Conveyor (6), and places it on a cart for distribution.

v) The Dispensing subsystem (9): An assembly of the tubes, valves, and control electronics, which dispense medicinal units into cups as the cups move along the Conveyor (6). This subsystem includes as few as a hundred, or as many as several thousand, tubes and valves, depending upon how many deferent medications are handled by the system (1).

(i) The Controlling Subsystem

Figure 2:
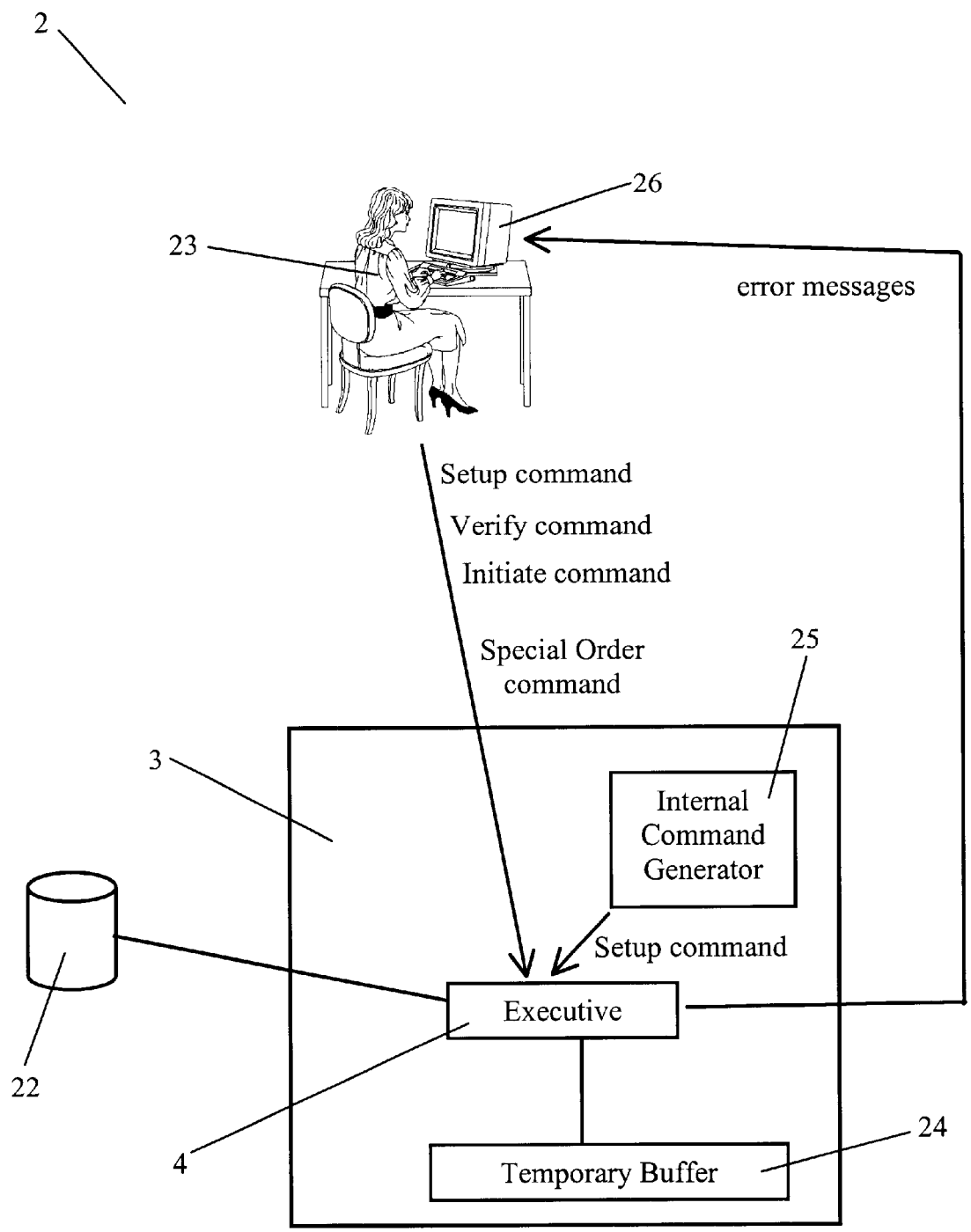
FIG. 2 shows a Controlling subsystem of the invention.

Referring to FIG. 2, the Controlling subsystem (2) consists of a Control Computer (3), a Database (22) of records containing information about the hospital's (or other institution's) patients—including their medication needs at each time of the day when medications are dispensed—and Controlling Software (hereinafter, the "Executive") (4) that runs on the Control Computer (3). The Executive (4) accesses and alters records of the Database (22), responds to various commands, and controls the other HDDS subsystems. The Executive (4) has logic, or accesses external software, to prevent dispensing of conflicting medications to a given patients. A medications conflicts if the patient is allergic to it or it should not be taken by the patient in combination with another medication that the patient is taking. When a patient's record in the database is updated to include a new medication, or a special manual order for certain medication is requested (see "Manual Mode" below), the Executive checks whether the new medication conflicts, and if so, refuses to update the patient record to include the new medication unless overridden by an operator (such as a physician) with authority to do so.

The commands to which the Executive (4) responds are either issued by an operator (23) or automatically generated by an internal command generator (25). They include the following commands:

The Setup command. When the operator (23) determines that a run of the system is necessary, he or she issues a Setup command to the Executive. Alternatively, or additionally, the Setup command is automatically generated by the Control Computer's (3) Automatic Command Generator (25) at one or more selected times of the day. The Executive (4) responds to the Setup command by searching the Database (22) and determining from the records therein the set of patients presently needing medications, which medications they need, and in what amounts. The list of patients and their prescriptions are sorted according to the patients' locations in the hospital: all the patients in the same nursing station are grouped together. Within such a group, the patients are preferably sorted according to room. Upon storing such information in the Control Computer's (3) memory in a Temporary Buffer (24), the Executive (4) is poised to initiate a run of the system in which cups are labeled, loaded with medications, sealed and placed upon carts to be distributed to hospital patients.

The Verify command. When the above has completed, the operator (23) verifies the results, if necessary, by issuing a Verify command. The Executive (4) responds to this command by making available the contents of the Temporary Buffer (24) for review and alteration. The operator (23) alters the contents if he or she determines that an additional patient should be included in the present run, that an included patient should be excluded (say, because the patient has left the hospital), or that an included patent's prescription should be modified. Performing such alterations requires entry of a password, which is only known to hospital personnel with authority to make such alterations. Once verified, the contents of the Temporary Buffer (24) correctly reflect the medicinal needs of the patients to be served in the present run of the system.

The Initiate command. When the operator (23) issues the Initiate command, the Executive (4) sends a signal to the HDDS's other subsystems to begin operation. The Control Computer (3) makes available to the Loading/Labeling subsystem (5) the contents of the Temporary Buffer (24), on a read-only basis.

The Special Order command. This is used to fill a special order for a single patient when the HDDS is operated in manual mode, as discussed below.

The Executive (4) runs continuously. As discussed below, the Executive (4) responds to other events besides the above-enumerated commands, as such events occur. Those events, together with the Executive's (4) response to each, are described below in the discussion of the other subsystems of the invented HDDS.

(ii) The Loading/Labeling Subsystem

Figure 3:
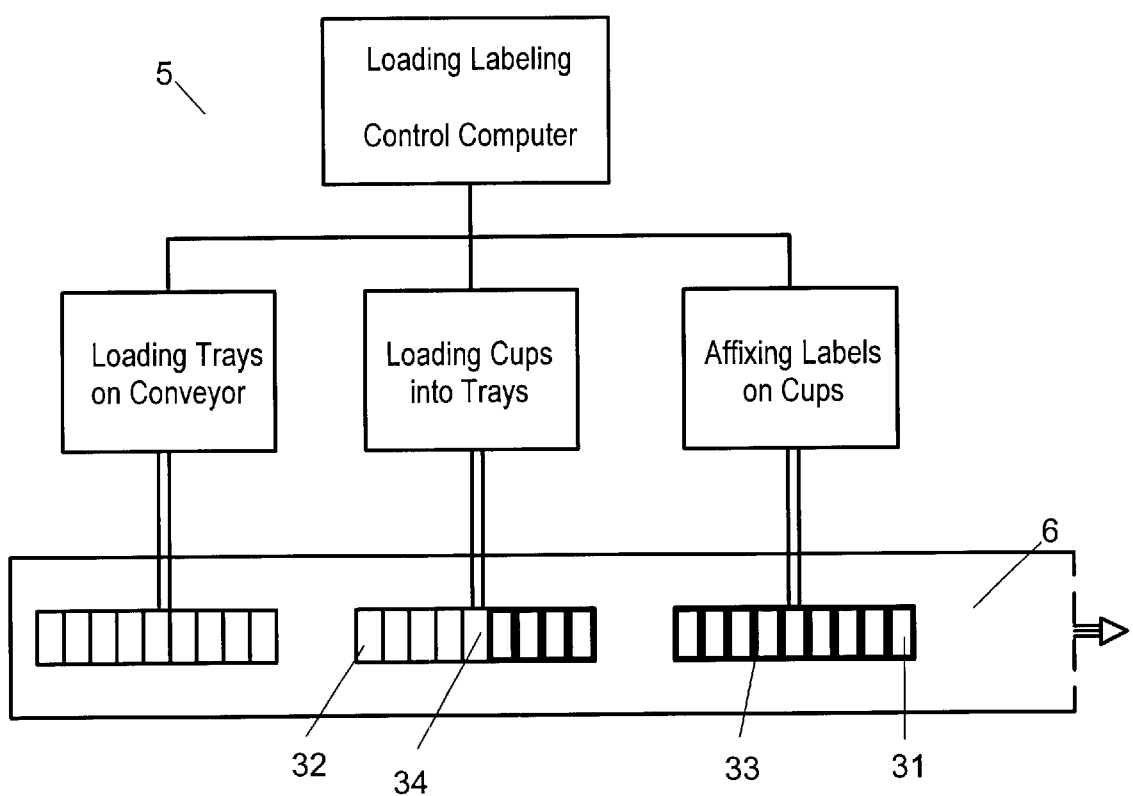
FIG. 3 shows a Loading/Labeling subsystem of the invention.
Figure 5:
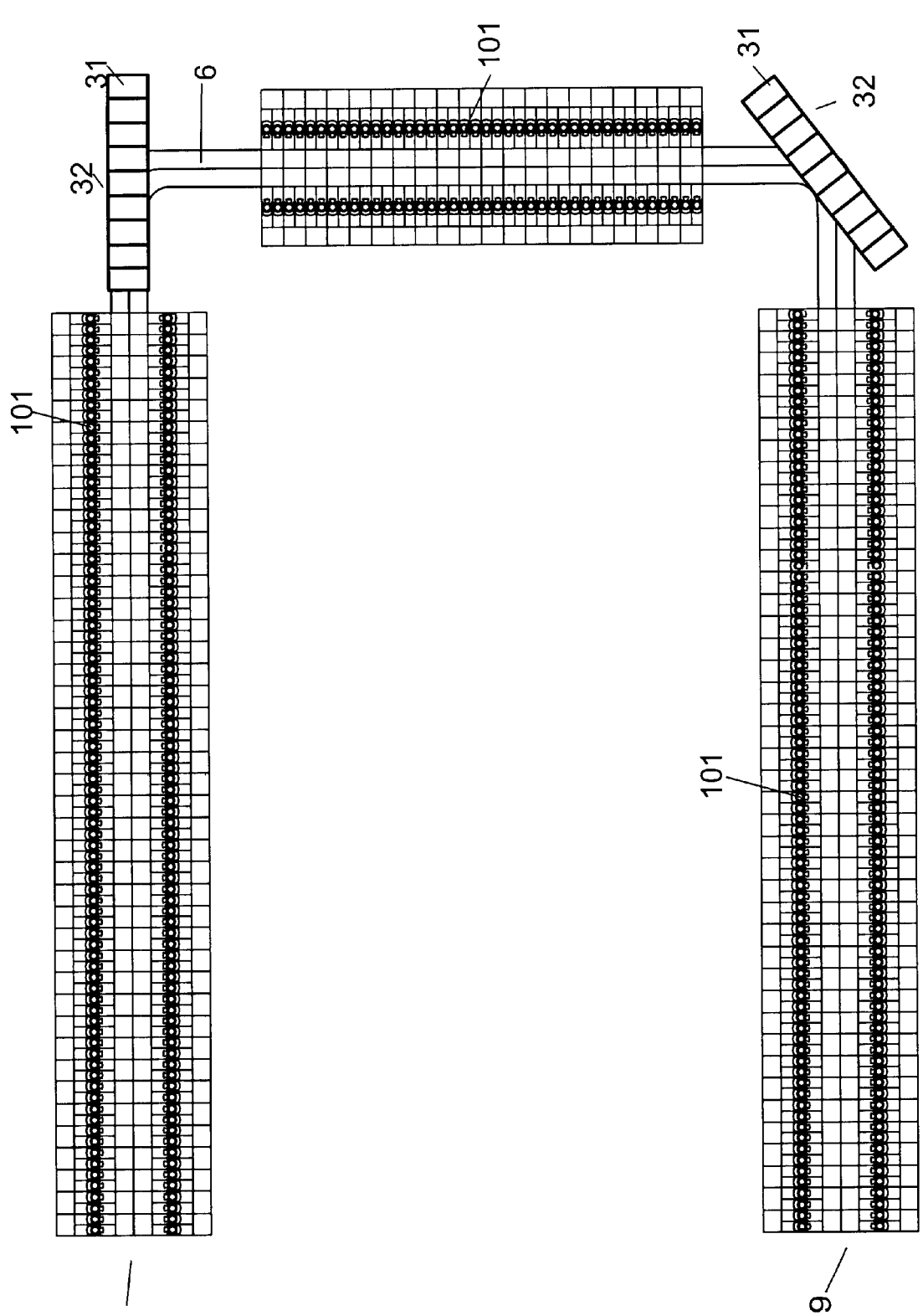
FIG. 5 is a plan view of the Dispensing subsystem of the invention, configured to dispense 1,000 different drugs.

Referring to FIG. 3, medication is delivered to each patient in a lightweight, substantially rectangular cup (31). To handle a large number of medication cups in an efficient and reliable manner, the Loading/Labeling subsystem (5) places each cup (31) in a special tray (32), preferably 9 to 12 inches long, with 9 to 12 cups per tray (32) (one cup per inch). Each cup (31) is preferably 0.95 inches long to allow a small amount of space (33) between cups (31). Each tray (32) is held fast to the Conveyor (6) at a single point (34) substantially at the center of the tray (32). This aids the trays (32) to proceed along the 90-degree turns of a U shaped system, as shown in FIG. 5, without rotating relative to the Conveyor (6).

In response to an Initiate command, the Executive (4) signals all other subsystems to begin operation. The Loading/Labeling subsystem (5) responds by starting the process of transferring trays (32) onto the Conveyor (6) and loading the trays (32) with cups (31). The Loading/Labeling subsystem (5) accesses the Temporary Buffer (24) to obtain the list of patients and their medications for the present run. Based upon such data, the Loading/Labeling subsystem (5) generates labels (35) for the cups (31) and affixes each label (FIG. 4, 35) to the side of one cup (31). The labels are placed on the cups after the cups are loaded onto the tray which is on the Conveyor (6). This is possible because the tray has an open side (FIG. 4, 46) which allows access to the sides of the cups on it. Once the cups are thus labeled they begin their journey underneath the Dispensing subsystem (9) in step-and-stop fashion.

The Loading/Labeling subsystem has three "stations" that work in parallel for efficiency of operation. In the Tray-Placement Station, a tray is transferred onto the Conveyor (6) during a "stop" phase of the step-and-stop motion of the belt. Thus, if there are places for nine cups on a tray, every ten steps of the Conveyor (6) there is a holder for a tray, and the Tray-Placement Station places a tray on the belt by inserting its holding means into the holder. There is always some space between two adjacent trays to allow the trays to turn on a U-shaped belt without their corners colliding. Thus, there is approximately one cup's width of space between each pair of trays.

When that tray reaches the Cup-Placement Station, cups are placed on the tray, one cup at a time. When the Conveyor is in a stop phase, the Cup-Placement Station places a cup on the tray, and then waits for the tray to step-and-stop again, and then places another cup in the next slot on the tray, and so on, until the tray has completely passed through the Cup-Placement Station, at which point it is full of cups.

In the Cup-Labeling Station, indicia (in print and barcode format) of the date and time, and the patient's name and location are placed on the side of each cup via a label or other printing means (such as ink jet). The patient's drug prescription—including the drug and the number of units required—is also displayed on the side of the cup in barcode format. Placing of such data on the side of each cup is done one cup at a time: a label is placed on the first cup on the tray during a stop phase, and then when the Conveyor steps-and-stops again, a label is placed on the second cup on the tray, and so on, until all cups on the tray are labeled. The order of labels is determined by the sorted list in the Control Computer's (3) Temporary Buffer (24). At that point the tray is ready to start passing under the drug tubes for dispensing of medication, as described below.

Figure 4A:
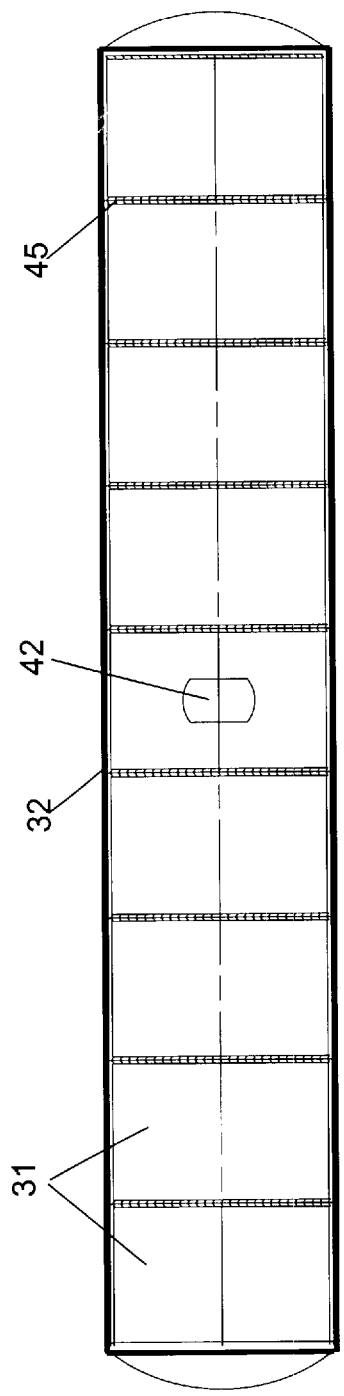
FIG. 4a shows a top view of a tray for holding medication cups according to the invention.
Figure 4B:
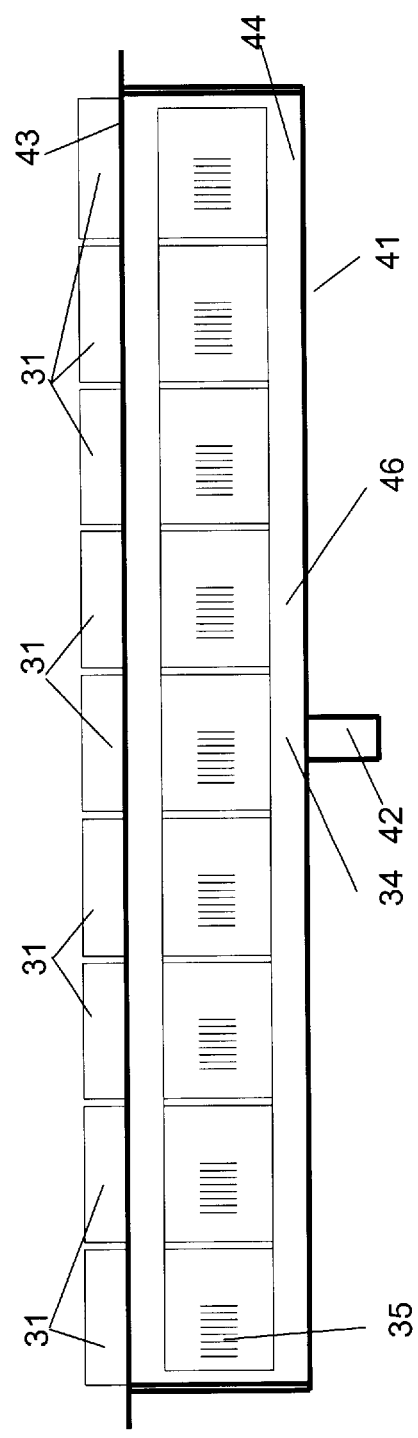
FIG. 4b shows a side view of a tray for holding medication cups according to the invention.

Referring to FIGS. 4a and 4b, a tray (32) for nine cups (31) is illustrated. The tray (32) comprises a top surface (44), as well as a bottom surface (41) having a holding member (42) protruding downward therefrom substantially at the tray's center point (34), to hold the tray (32) to the Conveyor (6). The holding member (42) is preferably substantially rectangular in cross-section so that the tray (32) does not rotate while held to the Conveyor (6). The tray (32) also comprises outer bars (43) raised above the top surface (44), together with interior bars (45) to hold the cups (31) in position. The interior bars (45) thus form compartments into which the cups (31) are placed. At least one side (46) of the tray must be open (hence the need for bars instead of side walls) so that barcode readers of the dispensing means have line-of-sight access to the label (35) affixed to each cup (31), while the cup (31) is on the tray (32).

In one HDDS embodiment only one type of medication is placed in each cup. This facilitates recycling of unused drugs, as described below. In this embodiment the barcode that the Loading/Labeling subsystem attaches to the side of each cup contains the code and quantity of only one medication. In an alternate embodiment, all medications needed by a single patient are dispensed into the same cup, and there is only one cup per patient. In this latter embodiment, the label placed on the side of each cup has indicia of one or more medications needed by the patient, together with the required quantity of each such medication.

Occasionally a tray must be placed upon the Conveyor even though it is not filled with cups. This is the case if a tray is only partially full at the end of the run. But there is a scenario in which the Loading/Labeling subsystem must start another tray even though the previous tray is not full. This occurs where the next patient in the Temporary Buffer (24) is in a different nursing station from the previous patient, and hence, his or her cup must be placed on a different tray.

(iii) The Conveying Subsystem

Referring to FIG. 5, the Conveying subsystem (7) comprises a Conveyor (6) or other similar conveying means (hereinafter, the "Conveyor") that moves in step-and-stop fashion. The Conveyor (6) is adjustable to convey along a straight line or another shape. Preferably, it is configured in a substantially U-shape to reduce the length of the HDDS footprint.

Figure 6:
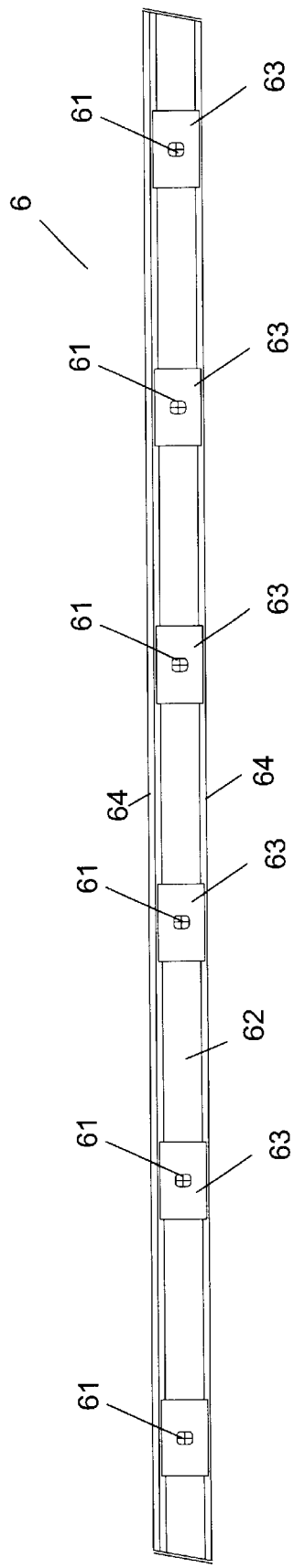
FIG. 6 depicts a chain-and-sleeve conveyor according to the invention.

Referring to FIG. 6, the Conveyor (6) includes a plurality of substantially rectangular holder carriages (63) or sleeves sliding on rails (64), each having a receptacle or depression (61) for receiving the holding member (FIG. 4, 42) of a tray (FIG. 5, 32). The Conveyor (6) is lightweight for ease of movement during the "step" portion of its step-and-stop motion. Accordingly, the Conveyor (6) preferably comprises a thin, lightweight, but strong, chain (62), with the aforementioned carriages (63) with depressions or sleeves (61). The depressions or sleeves (61) are spaced apart from each other the length of one tray plus one inch. Thus, in the case where trays hold nine cups each, they are ten inches apart. This leaves an inch between trays for ease of turning if the Conveyor (6) has any bends in it, such as when it is U-shaped. At the end of the Dispensing subsystem (9), the Conveyor (6) continues for sufficient length to facilitate the Sealing/Removing subsystem (8) to seal the cups (31), cover the trays (32), and remove the trays (32). The Conveyor (6) then loops underneath itself and returns to the beginning.

The trays are preferably a whole number of inches wide, one inch per cup, with the cups being 0.95 inches wide, thus leaving 0.05 inch between adjacent cups. The front of each tray placed on the Conveyor is one inch from the back of the previous tray, so that the last cup of one tray is 1.05 inches from the first cup of the next tray. Each tray preferably includes a ridge at the front and back ends for use by the Sealing/Removing subsystem to remove the tray from the Conveyor once the cups are sealed and the tray is covered. These ridges preferably extend laterally sufficiently to be helpful to the Sealing/Removing subsystem, but not so far as to cause tray collision during turns. Giving the ridges rounded corners aids in avoiding such collisions.

Figure 7:
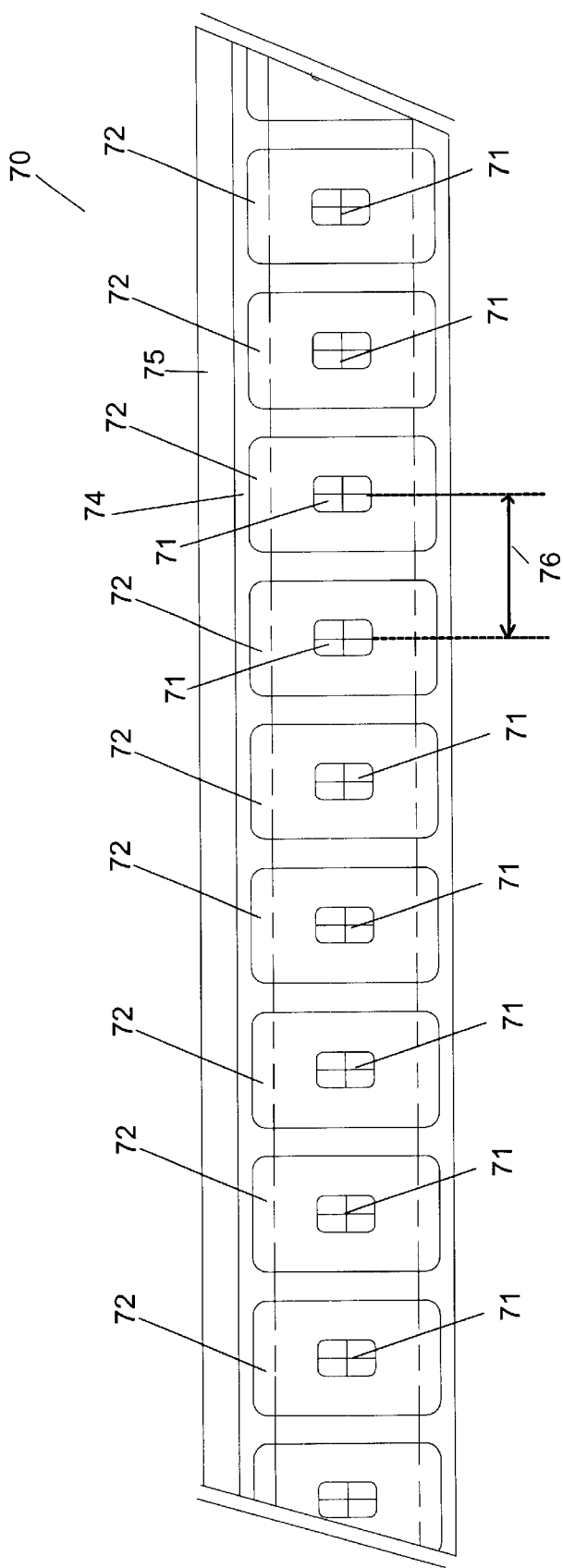
FIG. 7 depicts a sectional conveyor according to the invention.

Referring to FIG. 7, in an alternate embodiment the Conveyor (70) comprises a plurality of sections (72), each as wide as one medication cup, and each including a depression or sleeve (71) adapted to receive the holding member of a tray. The spacing (76) between the depressions is one cup width. The sections slide on rails (74) within the chain housing (75). The number of cups per tray varies, and hence, the length of the trays vary; still, each tray's length is a multiple of the width of one cup, and hence is a multiple of the width of one section (72) of the Conveyor (70). For some positive integer, n, the length of a tray capable of holding n cups equals n times the width of one section (72) of the Conveyor (70). For example, if a tray holds 11 cups, and the Conveyor sections are one inch wide, the tray is 11 inches long, and each cup fits within a one-inch span of the tray. Manifestly, each tray's holding member (42) must be positioned directly underneath one cup (and not in between two cups), so that it fits into the sleeve or depression (71) of a section (72) of the Conveyor (70). Therefore, each tray in this embodiment preferably holds an odd number of cups, so that its holding member (42) is at the center of its bottom surface (41). In this embodiment, trays of different lengths can be used in a single run of the system. In this embodiment, as in the above-described embodiment, there is the width of one section (72) of the Conveyor (70) between trays, for collision avoidance during turns.

In either embodiment, when the Executive receives an Initiate command, it assumes high-level control of the filling process from beginning to end. It starts by signaling the Loading/Labeling subsystem to place a tray onto the Conveyor at the Tray-Placement Station. When the first tray is so placed, the Loading/Labeling subsystem informs the Executive that one tray has been placed on the Conveyor. The Executive responds by signaling the Conveyor to move one step. The Conveyor moves one step, and awaits further instructions from the Executive. The Executive continues to signal the Conveyor to move a step until enough steps have been taken to place the tray at the spot within the Cup-Placement Station where a cup can be loaded onto the first position of the tray. At this point, the Executive signals the Cup-Placement Station to place a cup onto the tray. The Cup-Placement Station responds by placing a cup onto the tray at the first position and informing the Executive that it has done so. The Executive then signals the Conveyor to move one step, and when that has been done, signals the Cup-Placement Station to place another cup onto the tray, and so on, until the tray is loaded with cups. In the mean time, the Executive has also signaled the Tray-Placement Station to place another tray onto the Conveyor ten steps after the first tray was so placed (recall that each tray holds nine cups, and there is one inch between trays). As this stepping-and-stopping, loading of trays and loading of cups, is going on, eventually the first tray reaches a position of the Cup-Labeling Station where a label can be placed on the side of the first cup. At this point, the Executive signals the Cup-Labeling Station to do so, and when this has been done the Cup-Labeling Station informs the Executive. At this point, the Executive signals the Conveyor to move one more step, and when that has been done, signals the Cup-Labeling Station to label the next cup, and so on, until all cups on the first tray have been labeled.

Thus, the placing of a tray on the Conveyor, the placing of cups on the tray previously so placed, and the labeling of cups on the tray ahead of that one, all take place in parallel for maximum efficiency, as the Conveyor is stepping-and-stopping. Also taking place in parallel is the filling of the cups with medication, once they reach the point of the Conveyor where they are passing under the drug tubes. Thus, when the first tray, now full of labeled cups, arrives at a spot just underneath the first set of drug tubes, the system is in a position to start filling medication cups as an additional tray is being placed on the Conveyor, another is being filled with cups, and the cups on still another are being labeled. In this way, at each step, the Executive knows about certain tasks that must be completed by various parts of the overall system before the Conveyor can be signaled to more one more step. Included in this process, as well, are the filling of cups with medicinal units and the sealing and removing activities at the end of the Conveyor once the first cup reaches the end. As will be seen, as cups arrive beneath the medication tubes, the Executive does not signal the Conveyor to move another step until all medications to be dispensed into the cups been successfully dispensed. Likewise, as the cups arrive at the stations of the Sealing/Unloading subsystem, the Executive does not signal the Conveyor to move another step until all necessary sealing and/or unloading actions have been completed.

(iv) The Sealing/Removing Subsystem

Figure 8:
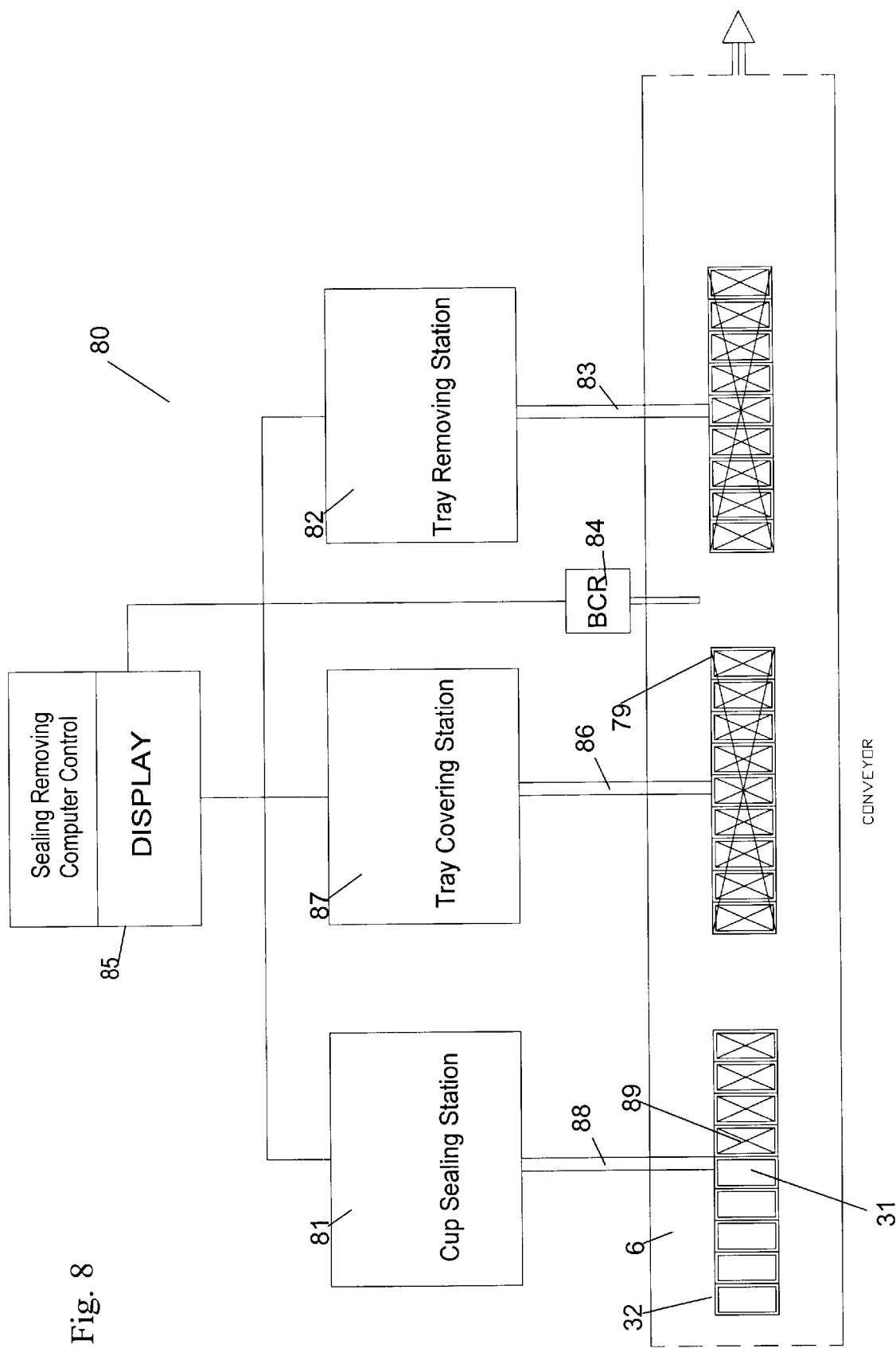
FIG. 8 shows a Sealing/Removing subsystem of the invention.

The range of activities taking place at each step includes tasks to be performed at the end of the Conveyor. When the cups emerge from underneath the drug tubes, having had all necessary medicaments dispensed into them, the cups are sealed and the trays are covered and removed onto a cart for distribution. When the Sealing/Removing subsystem has removed the last tray (and informs the Executive of such—see below), the Executive no longer signals the Conveyor to move another step, and the Conveyor halts. Thus, as shown in FIG. 8, at the end of the Conveyor (6) there is a Sealing/Removing subsystem (80) for sealing cups, and covering and removing trays.

There are three "stations" in this subsystem. The first is the Cup-Sealing Station (81), which includes a sealer (88) that places a plastic see-through seal (89) over the top of each medication cup to seal in the medication until the patient breaks the seal (89). At the time of such sealing, the cup (31) has passed beneath every drug tube. Like the Cup-Labeling Station of the Loading/Labeling subsystem, the Sealer (88) operates on one cup at a time, as the Conveyor (6) brings that cup into position.

After all cups on a given tray (32) have been sealed, the tray arrives at the Tray-Covering Station (87), which includes a Coverer (86) that places a cover (79) over the entire tray. This is helpful to protect against the cups dropping off the trays and to facilitate accurate grouping of the trays. The Coverer also places a label (not shown) on the cover containing indicia of the nursing station name and location, both in human-legible form and in barcode encoding.

Next, the tray arrives at the Tray-Removing Station (82) which includes a Remover (83). When the Remover (83) removes a tray (32) from the Conveyor (6), it notifies the Executive (4) of such. The Executive (4) maintains a count of the number of trays on the Conveyor at any given time. When the number reaches zero, the Executive no longer signals the Conveyor to advance a step.

The Sealing/Removing subsystem (80) includes a barcode reader (84) connected to a display (85). The attendant uses this barcode reader (84) to scan the barcode on the tray cover (79) once the Coverer (86) places such cover (79) on the tray (32). When the barcode is scanned, the display (85) displays indicia of the destination nursing station; from such information the attendant determines which cart (not shown) to place the tray on. Preferably, to reduce human error in placement of trays (32) onto carts, and ultimately, to nursing stations, the Coverer color-marks the tray covers (79) such that each nursing station is assigned a different color. If necessary, different carts are used for different nursing stations. In such event, the operator places trays (32) for each nursing station on a separate cart.

Each cart is also equipped with a Cart Barcode Reader, a Cart Display, and a Cart Computer operatively coupled to the Control Computer (FIG. 1, 3). To ensure error free delivery of medication to the patients, the attendant, using the Cart Barcode Reader, scans the barcode on each cup when the cup is removed from the tray. The patient name, location, and medication are displayed on the Cart Display. When the medication is ultimately delivered to the patient, the attendant enters affirmative indicia into the Cart Computer; otherwise, the attendant enters or negative indicia into the Cart Computer if the medication does not reach the patient. If the attendant enters negative indicia, he or she also enters indicia of the reason the medication was not delivered. This information is transferred to the Control Computer, which updates the patient's record(s) in the Database (FIG. 2, 22) accordingly. If the Cart Computer is coupled to the Control Computer via wireless communication, the transfer of information occurs immediately upon entry by the attendant. Otherwise, the information is stored in the Cart Computer and later uploaded to the Control Computer when the attendant brings the Cart to the Controlling subsystem. If the medication is not ultimately delivered to the patient, it is preferably recycled, and the hospital is entitled to credit for such medication from the drug refilling center (see below).

(v) The Dispensing Subsystem

Figure 9:
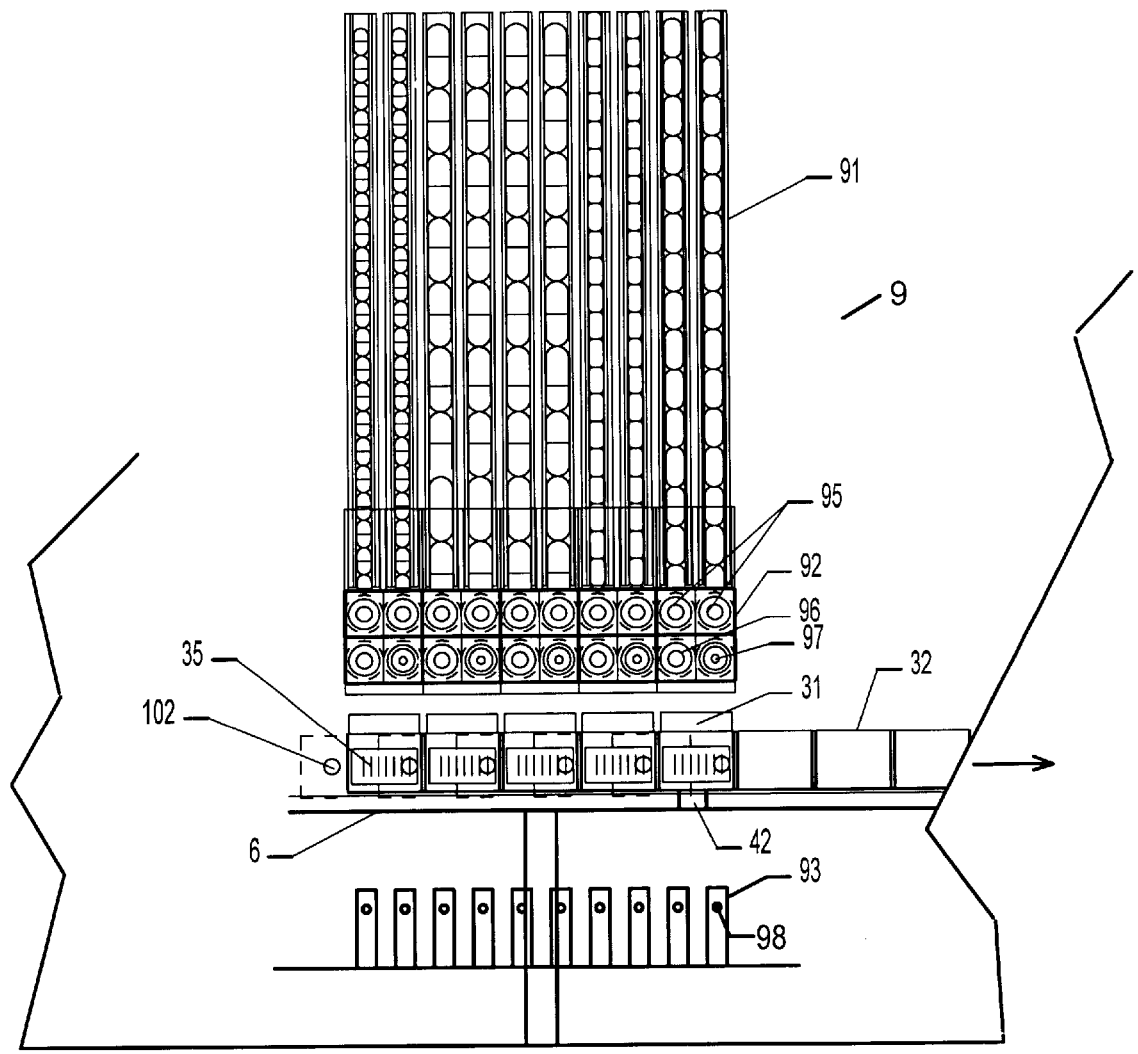
FIG. 9 is a fragmentary view showing a portion the Dispensing subsystem of the invention as seen from the front.

Referring to FIG. 9, the heart of the invented HDDS is a Dispensing subsystem (9). This subsystem includes hundreds or even thousands of tall, thin drug tubes (91) positioned side-by-side. Each drug tube (91) stores a plurality of medicinal units of a particular drug, and is coupled to a valve (92) for dispensing of the same. Each drug tube (91) has its own valve (92) for dispensing the drugs, and each valve (92) has its own control electronics (93) to control dispensing of drugs from the tube (91). These drugs are dispensed as the patients' cups (31) pass beneath the tubes (91) on the Conveyor (6). The row of vertical drug tubes containing the drugs to be dispensed, together with the dispensing valve for each, is hereinafter referred to as the "Tube Row" (94). Depending upon the embodiment of the dispensing tube/valve apparatus, each valve (92) of Tube Row (94) is integrated with the tube (91), or is detachable from the tube once the tube (91) becomes empty. If detachable, the empty tube is discarded or returned to the drug refilling center and is replaced with a full tube. If integrated, the integrated tube-and-valve are returned to the drug refilling center and replaced with a full, integrated tube-and-valve (ITV).

To ensure reliable and uninterrupted filling of the cups, each medication has a backup tube on line. Thus, for example, a system of one thousand different medications includes two thousand tubes and valves. Such is needed in case, in the middle of a filling cycle, one of the tubes runs out of medicinal units or malfunctions. In such event, the same medication is dispensed from the other (backup) tube, and the filling process to continues uninterrupted. The two tubes with the same medication stand side-by-side, and each has its own separate valve and valve-control electronics.

In an embodiment where the tubes are discarded, each tube disconnects from the valve upon which it sits, and is discarded when empty. Each valve, together with its control electronics, is not discarded when the tube becomes empty, as such would be wasteful. Instead, the tube is disconnected from the valve and a replacement tube with the same medication is attached in its place. The two identical valves—one for the active tube and the other for the backup tube—are constructed as a single unit, preferably one inch wide, minus approximately 10 mil for clearance between adjacent units.

Referring to FIGS. 10a through 10c, the two valves are called, collectively, a "valve-unit" (101), or a VU. Each valve (92) in the VU (101) is a half-inch wide (minus 5 mil), and each tube (91) that sits upon a valve (92) of the VU is approximately 0.4 inches wide.

Alternatively, each tube and its valve are permanently connected to comprise an integrated unit, called an integrated tube-valve, or ITV. Each such ITV is a half-inch wide, minus approximately 10 mil for clearance between adjacent units, so that when two stand side-by-side, the pair is one inch wide. Thus, either way, within a one inch wide span of the HDDS there is an active tube and a backup tube for the same medication, for smooth running of the overall system. The valves and tubes are arranged in Modules of, preferably, 50 VUs (or ITV pairs) per Module. Each Module has a Module Microprocessor that receives commands from and forwards data to the Control Computer.

The following description is directed to an HDDS using VUs (as opposed to ITVs) for dispensing drugs. The HDDS includes 1,000 different kinds of medication. Each medication has an active tube and a backup tube. The HDDS thus includes 2,000 tubes mounted on 1,000 VUs. The HDDS is composed of 20 Modules; each Module includes 100 tubes, as well as 50 VUs (each having two valves).

As noted, each VU is composed of two valves (92) with one tube (104)(107) coupled to each valve. Each VU is connected to a barcode reader (102), positioned in front of the valves. The two valves of each VU share the barcode reader (102). Each VU has a Memory Buffer (103) containing the numerical code of the drug in its tubes. Each VU's barcode reader (102) is coupled to control electronics (93) that operate the VU's valves (92). The barcode reader (102) for the VU reads the barcode of a cup (31) that is about to arrive under the VU, or has just arrived under it. If the barcode reader uses a "point" type scanner, it is positioned just ahead of the 'stop' point of the cup, so that it scans the cup as the cup moves toward its stop point. Thus, by the time the cup comes to a stop and is ready to receive medicinal units, the barcode reader has read and decoded the entire barcode. If, however, the barcode reader uses a "wide-beam" type scanner, the barcode reader is positioned adjacent to the cup's stop point, so that when the cup stops under a drug-dispensing valve (92), at that point the barcode reader scans and decodes the entire barcode. No matter what type of barcode reader is used, once the barcode data is scanned and decoded, it is immediately forwarded to the VU.

As noted, each valve of a VU has its own control electronics (93), including a Memory Buffer (103) for storing the code of the drug in the tube, and an "active" light (98) for showing whether the valve is currently active (see below). The VU's barcode reader transmits the decoded barcode data to both valves' control electronics. Each valve's control electronics contains in its Memory Buffer indicia of whether the valve is in the active state. In particular, the Memory Buffer contains a value indicating which status the valve is in (active, backup, empty, or malfunctioned). The active valve is that valve whose memory contains indicia that the valve is currently in 'active' status. The active tube is the tube connected to the active valve. If the valve is active, its active light (98) is on, otherwise its active light (98) is off. When the active valve's control electronics receive the medication code(s) and quantity(s) to be dispensed into the cup below, it determines whether its drug code corresponds to any of the drug codes forwarded to it. (If there is only one drug per cup, then only one drug code and quantity are forwarded to it at each 'stop' phase of the 'step-and-stop' cycle.) If there is no match, the active valve signals the Control Computer that it will not dispense during this 'stop.' Otherwise, it dispenses the appropriate number of medicinal units (108), and then signals the Control Computer that such dispensing has completed. When the Control Computer receives a signal from each active valve in the system, it knows that all dispensing is complete. It then waits a certain interval of time to assure that all drugs so dispensed have fallen down through the funnels and into the cups. After this, when all other activities required during the present 'stop' phase are also complete—to wit, loading or labeling of cups, sealing of cups, unloading of trays, etc.—the Executive triggers the Conveyor to move another step.

When the active tube runs out of medication or the active valve malfunctions, the active valve "passes the baton" (transfers active status) to the backup valve for that drug. This may happen in the middle of when the active valve is dispensing drugs into a cup. For example, if three medicinal units are required in the present cup, and the active tube (107) has only two units left, the active valve must transfer active status to the backup valve (104) after dispensing the two units into the cup. The active valve accomplishes the transition by altering the status indicia within its own Memory Buffer to indicate "inactive," signaling the backup valve to become active, and forwarding to the backup valve the number of medicinal units yet to be dispensed into the cup stationed below it. The forwarding of the number of medicinal units still to be dispensed is necessary because, as noted, at the time the previously-active valve transitioned to non-active status, there were still possibly one or more medicinal units remaining to be dispensed into the cup. Thus, when the backup valve takes over as the newly-active valve, it may have to complete the job begun by the previously-active valve vis-a-vis the current cup. When the previously-active tube (107) is replaced with a full drug tube (or the previously-active valve cleared of its malfunction, as the case may be), the previously-active tube (107)/valve becomes the backup tube/valve for that medication within the HDDS.

The data decoded by the decoder is forwarded to the control electronics of both valves of the VU which include a Memory Buffer for holding the code of the drug inside the tube. The data transmitted by the decoder includes the code of the medication(s) to be dispensed into the cup, as well as the number of units of such medication(s). If the code of the drug to be dispensed corresponds to the code of the drug stored in the valve's above-referenced Memory Buffer, and if the valve is in active status, the valve dispenses the required number of units into the cup. Thus, although each valve has its own control electronics, the two valves of a valve-unit are operatively connected such that each valve communicates with the other valve to shift active status to the other valve. Accordingly, when active status is so shifted, the backup valve that becomes active becomes the primary valve, as discussed above. When the operator replaces the empty tube (see below), the HDDS again has a fully-stocked backup tube for that medication.

Referring to FIGS. 11a–c, to make the drug distribution system compact, pairs (110) of VUs—(118) and (119)—and/or ITVs (as the case may be) are mounted back-to-back, that is, across from one another, and all the VUs or ITVs are hence arranged in two parallel rows (see FIG. 5). Each of the two such VUs or ITV pairs positioned back-to-back dispenses a different medication. There is a single funnel (111) for the two VUs or ITV pairs, and hence, in the system there are half as many funnels (111) as there are VUs (118) and (119), and one quarter as many funnels (111) as there are drug tubes (104)(107)(112) and (113).

In the present system, with 2,000 valves and 1,000 valve-units or 2,000 ITVs, there are 500 funnels. The two valve-units positioned back-to-back share the same barcode reader (102), decoder and funnel (111). When the cup (31) arrives under the funnel (111) opening (112), the shared barcode reader (102) reads the barcode (35) from the side of the cup (31), and the decoder transmits the code and quantity of drug required by the patient to the control electronics (114) to (117) of all four valves sharing the decoder. Each valve, via its control electronics, independently determines whether to dispense any drugs into the cup. The valve dispenses drugs only if it is in the active state and the drug code on the cup corresponds with its own.

If, to allow for recycling of unused drugs, only one medication is dispensed into each cup (i.e., one or more units of the same medication), then two valves sharing the same funnel never dispense medicinal units into the same cup at the same time. If, however, there is only one cup per patient, multiple medications may be dispensed into the same cup, depending upon the patient's medication needs, such that the patient ultimately receives a "cocktail" of medications in the single cup distributed to him or her. In that case, the barcode that the Loading/Labeling subsystem attaches to the side of each cup contains the codes and quantities of all medications needed by the patient. In such scenario, two of the medications needed by a patient may be stored in tubes arranged across from each other in the same VU pair, and hence share a funnel. In that event, two valves sharing one funnel dispense medicinal units at the same time when the cup for that patient arrives underneath it. The funnel opening (112) is wide enough to allow such simultaneous dispensing without the possibility of the medications jamming inside the funnel. (Alternatively, the module's microprocessor arranges for one of the valve-units to delay dispensing until the other one is finished.) The tops of the cups, in turn, are at least as wide as the funnel opening, so that no medicinal units fall outside the cup.

Referring again FIG. 5, a plan view of an HDDS arranged in a U shape is shown. In an HDDS with 1000 different drugs, the total length of the U-shaped path through the HDDS is five hundred inches, or approximately 42 feet. An HDDS arranged in such manner, and having 1000 drugs, has a footprint approximately 17 feet long and approximately 7 feet wide.

Notably, however, if multiple medications that are dispensed into the same cup are not ultimately used by the patient, they cannot be recycled in an efficient, error free and cost-effective way, as each medication has been mixed in with other medications. This can be a significant disadvantage, as a substantial number of drugs dispensed each day in a hospital setting are not used by the patient. Accordingly, in the preferred embodiment of the invented system only one medication is dispensed into each cup, and one or more cups are distributed to each patient. If more than one cup is distributed to a given patient, such cups are arranged consecutively on a tray for filling.

If the drugs are not used and the seal on the cups remains intact, the hospital recycles the drugs by returning them to the drug refilling center, where the drugs are removed from the sealed cups and placed into the general pool of drugs of the same type for filling into drug tubes. Prior to returning the unused drugs to the refilling center, the hospital (or other institution such as a nursing home) updates the patient file to reflect that the patient did not use the drugs. Then the hospital places the cups with the unused medication in special boxes and sends them to the drug refilling center together with the empty tubes or ITVs (as the case may be) that the hospital returns to the center on a daily bases. At the center, which services a number of hospitals, the returned unused drugs are sorted automatically using the encoded information on each cup's label, and returned to the main stock for future use. Each hospital is credited for the returned unused drugs.

Several advantages to the above scheme should be apparent. For example, it should be apparent that numerous cups can each be filled with drugs simultaneously, as the cups are positioned in single-line fashion and make their way along the Conveyor, stopping under each valve-unit. It should be apparent, moreover, that there are economies of scale, as the second and subsequent cups are filled simultaneously with the filling of the first cup during the step-and-stop of the Conveyor. Further, new medications can be added to the overall system by increasing the system's length, and not its complexity.

Preferably each VU includes, for each valve, an "empty-indicator means" (95)—such as a light-emitting diode—to indicate that the tube connected to that valve has run out of medicinal units. When a drug tube becomes empty during system operation, and control is passed to the backup valve in the VU, the VU activates its empty-indicator means (95) associated the empty tube to alert the attendant that the tube needs replacement. The valve-unit also sends a signal to the Control Computer, which preferably displays a message regarding the tube being empty, and prints a re-order notice. Preferably, as well, the Control Computer automatically (over a computer network) orders from the drug refilling center a new tube of the same drugs. If such automatic reordering is not performed by the Control Computer, hospital personnel reorder the drugs electronically by any means known to one skilled in the art (such as by email), or transmit the printed reorder notice—preferably by facsimile transmission—to the drug refilling center. Additionally, it is preferable that, if the HDDS supports a manual-mode of operation (see Section 3 below), each VU includes, for each valve, a "signal means" (96)—again, such as a light-emitting diode (preferably of a color different from that of the empty-indicator light)—to indicate that the tube connected to that valve is involved in the present special order being filled manually. As discussed below, when a special order is initiated by the attendant, the Control Computer (3) signals all VUs involved in the order, and each such VU activates the signal light (96) associated with its active valve to alert the attendant that the VU is involved in the special manually-filled order.

An example is now provided to demonstrate the speed at which the HDDS fills hundreds of cups with the necessary medications. In this example, the HDDS has 1,000 different kinds of medication and the system fills 1,000 cups per run. The system includes 1,000 VUs and 2,000 tubes, arranged in two rows, back-to-back, as shown in FIG. 5. The system could equally have 2,000 ITVs, arranged in 1,000 ITV pairs, in place of the 1,000 VUs. For purposes of this example, however, we will assume the system uses VUs instead of ITVs. There are 500 steps in the step-and-stop journey of each cup. In each stop, the cup is positioned under two different medications, which share a funnel, and at most one of such medications is dispensed into the cup (here it is assumed that there is only one drug per cup). The system is arranged in a U-shape as shown in FIG. 5. The length of the U-shaped track is 500 inches.

Manifestly, the duration of the stop time of a "step-and-stop" cycle must be at least as great as the time it takes the medicinal units to fall into the cups. Preferably, the distance from the bottom of the valve to the bottom of the cup is no more than four inches, in which case the system waits 0.2 seconds from the moment the last medicinal unit is released from a valve until the Conveyor moves the cups to the next VU. The duration of the 'step' time must be at least as great as the time it takes to reload the valves that discharged in the previous step. The longest capsule is approximately 0.85 inches long, thus necessitating approximately 0.185 seconds to reload. Because the stop time is greater than that, however, the duration of the step time is not limited by the reloading mechanism, and is hence determined by the reading speed of the barcode reader, assuming a "point" type barcode scanner is used. The speed of the Conveyor during the step phase must be less than 30 inches per second, which is the upper limit for that type of barcode scanner. If the step time is increased to 0.1 seconds for a speed of 10 inches per second, the total time to move the cups past one VU is equal to 0.1 (step)+0.2 (stop)=0.3 seconds. To fill 1,000 cups in a system of 1,000 VUs, the 1,000 cups are arranged on 112 trays, where a maximum of nine cups fit on each tray. Thus, the Conveyor takes 1611 steps to fill all 1,000 cups (there is one one-inch space between each pair of trays, for a total of 111 such spaces). The minimum time to fill 1,000 cups is therefore 0.3×1611=483.3 seconds or approximately eight minutes.

In reality, the duration of one filling period is determined by the speed of the Loading/Labeling subsystem on the front end—trays are still being placed on the Conveyor and cups are being loaded onto trays and labeled—and by the speed of the Sealing/Removing subsystem at the back end, as soon as the first tray reaches the end of the Conveyor and its cups must be sealed, and the tray covered and transferred to the carts. The present example also assumes that the indexer which moves the Conveyor can move ten inches per second, which may or may not be true. This depends upon the total mass of the Conveyor, plus the trays, cups and medications being moved by it. Assuming the Labeling/Loading subsystem requires approximately one second to handle one cup, the stop time is increased to one second and the step time remains 0.1 second. The total time to fill one thousand cups is then 1.1×1611=1722 seconds, or 29.5 minutes. In this example the Sealing/Removing subsystem has 11 seconds to remove each tray. The duration of the stop time in the first 500 step-and-stop cycles (not counting the step-and-stop cycles necessary for the Loading/Labeling subsystem to prepare the first tray for its journey underneath the drug tubes) is determined by the Loading/Labeling subsystem, as during those steps the Sealing/Unloading subsystem is idle. The duration of the stop time in the subsequent 1,111 step-and-stop cycles is determined by the Sealing/Removing subsystem, as the first tray reaches the end of the Conveyor five hundred steps after it begins.

3. Manual Mode HDDS

The above discussion is directed to an automatic mode of operation of the HDDS. Automatic mode is used to efficiently fill a large number of medication cups, usually at pre-selected times of the day. Preferably, the HDDS according to the present invention is also operable in a manual mode. Manual mode is used to fill special, small-volume orders at any time of the day. Each such order is for one patient, and hence, there is one cup involved in each special order.

When filling a special order, there is no concern to recycle unused drugs, as the special order is for a patient known to be in the hospital. Hence, all drugs required by the order are placed in one cup. The attendant begins the process of filling the special order by issuing a Special Order command to the Executive, which places the system into manual operation. The attendant places a medication cup in the Cup-Labeling Station, and enters into the Control Computer indicia of the patient's identity, as well as indicia of the drugs and quantity of each required by the order. The Executive searches the Database for a record of the patient and retrieves from the database data regarding that patient's location and other patient status information as needed. If the patient is not found in the database, the Executive produces an error message to the console (FIG. 2, 26) informing the attendant that there is no patient matching the entered patient indicia.

If the patient is found in the database, the attendant enters indicia of the required medications and quantities of each. The Executive checks whether any of the entered medication conflicts for that patient (see above). If so, the Executive produces an error message to the console (FIG. 2, 26) informing the attendant that there is a conflict, and that special authorization is required to proceed with the order. If no conflict is found, or if the special authorization is provided, the Executive forwards the indicia of the medication(s) and quantity(s) to the Loading/Labeling subsystem, which generates and attaches to a cup a label indicating the required drugs' codes and quantities, including a barcode encoding of such data. The Executive also sends to the microprocessor of each module of the Dispensing subsystem an indication that a special order is underway, together with indicia of the list of drugs (and quantity of each) to be dispensed in fulfillment of the order. Each such module of the Dispensing subsystem forwards the list to all VUs in the module. Each VU checks whether its drug code matches any drug code involved in the special order. If so, the VU turns on its Signal Light (96), places itself into manual discharge mode, and stores in its Memory Buffer (103) indicia of the quantity of medicinal units to be dispensed from the attached tube.

The attendant places the cup upon a special cart having a barcode reader connected to a display. Using the cart's barcode reader, the attendant scans the side of the cup, which, as noted, contains a label with indicia of the medications involved in the order. The cart's display provides indicia of the locations of the VUs needed to fill the order. The attendant then walks the cart to the each such VU in turn, places the cup underneath the funnel where the medicinal units are discharged, and presses a "manual-mode discharge" button (97) on the VU. If the VU is in manual discharge mode (as indicated by its Signal Light), the VU discharges the required number of medicinal units, reverts to automatic discharge mode, and turns off its Signal Light (96). In this way, the attendant cannot obtain from the VU more than the dosage of that medication required by the order.

The attendant repeats the above process for each VU having a Signal Light on. Only when all signal lights are off has the order been filled, and the cup now contains all the medication, in the correct quantities, for the patient. If two or more patients require special orders, the attendant repeats all of the above steps for each patient. The attendant then distributes to each patient the appropriate cup containing the medications.

In one embodiment, the attendant begins the process of manually filling a "batch" of several special orders by issuing a Request Special Orders command issued to the Executive. Upon receiving such an order, the Executive prompts the attendant for the special order data (i.e., the patient's identity and required drugs and quantities of each) of the first special order in the batch. The Executive then assigns a unique "special-order ID" to that order and prompts the attendant for the data of the next special order. This process continues until the attendant responds to the Executive's prompt by indicating that there are no more special orders in the batch. The Executive stores in the database a record associating each special-order ID with indicia of the patient's identity, date and time, and the other special order data, as well as an indication that the special order has been requested but not yet filled. The Executive forwards the data for each special order, including the special-order ID, to the Loading/Labeling subsystem. That subsystem loads trays to capacity (rather than sorting them by nursing station as in automatic mode), and then generates a label for each special order in the batch, attaching each label to a separate cup thus loaded. The label for each order indicates the special-order ID, patient, and required drug(s) and quantity(s). When the Loading/Labeling subsystem has loaded the tray(s) with all the special order cups (one cup per special order), the attendant transfers the tray(s) onto the special cart. At this point, the Request Special Orders command is complete, and there is now a record for each such order in the database; at this point, each record indicates that the special order has been requested, but not yet filled.

The attendant fills each requested special order by causing a Fill-Special-Order command to be generated for each order, and filling the corresponding cup with the required medications, as follows. First, the attendant chooses a cup from the tray(s) on the cart and scans the cup's barcode with the cart's barcode reader. Upon reading the barcode, the cart's barcode reader transmits to the Control Computer a Fill-Special-Order command, containing indicia of the special-order ID to be filled. The Executive retrieves from the database the record for that special order, including the set of medications and quantities involved in that special order. If the record indicates that the order has been requested but not yet filled, the Executive forwards the medication and quantity data to each module of the Dispensing subsystem. As with the single-special-order embodiment described above, the appropriate VU(s) of the Dispensing subsystem turn on a Signal Light (96) and place themselves into manual discharge mode to await the pushing of the manual discharge button (97). The attendant walks the cart to the VUs with a Signal Light turned on, and pushes the manual-discharge button (97) to fill the cup as before. When each VU involved in the special order has dispensed its drugs and transitions out of manual mode, it also transmits an indication of such fulfillment back to the Executive. When the Executive detects that all drugs involved in the special order have been dispensed, it modifies the database record for that special order to indicate that the order has been filled. When one special order is filled as described above, the attendant scans and fills the next cup, and so on, until all cups are filled. Then the attendant distributes the medication cups to the appropriate patients.

In one embodiment, upon receiving the full set of special orders to be filled, prior to causing the Loading/Labeling subsystem to generate any labels, the Executive sorts the special orders according to the positions in the assembly of the drug tubes involved. If possible, the Executive sorts the orders to minimize the amount of walking the attendant must do. For example, if each order only involves one medication, the Executive sorts the orders according to the placement of the drug tubes within the assembly of tubes and valves.

4. Centralized-Control HDDS

The invented automatic-mode HDDS, as described above, utilizes decentralized control to some degree. In particular, the decision whether to dispense at each stop of the Conveyor is made locally by the control electronics of each valve, based upon information supplied to it by a barcode reader and decoder located at the VU (or ITV, as the case may be). In an alternate embodiment of the HDDS, all such control is exercised centrally at the Control Computer. The inherent tradeoff involved in shifting most of the decision-making, even as to local events, to a central "command" module (in this case, the Control Computer, and more particularly, the Executive), is that, while it adds complexity to the Executive, it also increases the flexibility of the overall system. In particular, more than one VU or ITV pair for the same drug can more easily be included in the Dispensing subsystem without being located adjacent to one another. Another benefit is that it reduces the number of individual barcode readers and decoders in the system, as it is no longer necessary to place such components at each VU or ITV pair.

In the centralized-control HDDS the Executive is structured in essentially the same manner as with the decentralized-control HDDS: it runs continuously, accesses the database as necessary, and responds to the same commands. The main difference is in the communications between the Executive and the valves of the Dispensing subsystem. The Executive maintains a record of the number of modules included in the HDDS, and the number of ITVs or VUs in each module. The Executive assigns a unique positive integer to each position within the Dispensing subsystem from which drugs are dispensed. The numbers range from 1 to i, with the first stop of a cup being at position 1 and the last being at position i. Thus, i is the number of stops that the Conveyor makes during one cup's journey underneath the drug tubes of the Dispensing subsystem. Assuming there is a funnel at each such position in the HDDS, i is also the number of funnels in the system. Thus, in the above example, where there are 20 Modules of 100 tubes each, there are 50 VUs and 25 funnels per Module. There are 20×25=500 funnels, and hence, 500 positions along the Conveyor where a cup stops under a funnel; each position is assigned an integer in sequence from 1 to 500. The first funnel is at position 1, and the last funnel in the journey is at position 500. If a module is added or removed from the system, the Executive reconfigures its data structures to account for the added or removed positions. In every case, after the addition or removal of a module, the positions that drugs can be dispensed from are numbered 1 through i, as before, but with a different value for i. At each position 1 through i, there are four slots, preferably designated (a) through (d), where the tubes reside. The VU at the outside of the U shape has slots (a) and (b), with slot (a) being on the right; the VU at the inside of the U shape has slots (c) and (d), with slot (c) being on the right when looking at the back-to-back VUs from the outside of the U. Thus, the Executive maintains data structures that store, for each position 1 through i, the drug code and quantity remaining of the tube at slots $1(a)$, $1(b)$, $1(c)$, $1(d)$, $2(a)$, $2(b)$, $2(c)$, $2(d)$ and so on, up to $i(a)$, $i(b)$, $i(c)$, and $i(d)$.

As the system operates, cups are filled with medicinal units, drug tubes are removed, drug tubes are installed, and occasionally a new module is added or a module is removed from the system. When any of these changes happens, the Executive modifies its data structures accordingly, so that at any given moment it has an accurate record of the code of the drug stored at each slot in the system, and the number of units left inside the tube at that position.

As with the decentralized embodiment, there is a set of control electronics associated with each valve in the system. Moreover, each drug tube—whether suitable for installation into a VU or part of an ITV—includes a microchip containing indicia of the code and number of medicinal units of the drug inside the tube. When a drug tube is installed in the Dispensing subsystem, the valve's control electronics reads its drug code and quantity from the microchip, and transmits the same to the Executive in the form of an Install-tube command, which includes indicia of the slot where the tube was installed. The Executive responds by updating its data structures to reflect the tube's position, drug code and quantity remaining (which is initially the quantity in the tube at installation). When a tube is removed, the control electronics for the corresponding valve transmit to the Executive an Uninstall-tube command, which includes indicia of the slot where the tube was removed. The Executive updates its data structures to reflect that there is no tube currently installed at that slot.

As previously noted, each VU contains two tubes with the same drug; typically, as well, in a system that uses ITVs instead of VUs, each tube in a pair of side-by-side ITVs dispenses the same drug. For each such pair, one tube is the active tube and the other is a backup tube. For reasons that will become clear below, for each VU or pair of ITVs, the Executive maintains an indication of which is the active tube.

When a "run" of the HDDS takes place, a set trays is placed onto the Conveyor, loaded with cups, and the cups are then labeled, as described above. The Executive coordinates the activities of the different subsystems. It begins by causing the Loading/Labeling subsystem to place the first tray onto the Conveyor and load it with cups, and label the cups. The Executive then instructs the Conveyor to advance the correct number of steps so that the first cup on the tray is in position 1, that is, under the first funnel of the system. The subsequent step-and-stop motion of the Conveyor, together with the dispensing action of the valves, is controlled by the Executive. The Executive maintains data structures that record, for each order in the run, an indication of what position on the Conveyor the cup(s) for that order are located. Note that when a tray is loaded with cups and the cups are labeled, the cups are not under any funnels immediately; they can be thought of as being at positions 0, −1, −2, −3, etc. With each step of the Conveyor, their position is incremented by one. The Executive also tracks, for each cup, the medication(s) and quantity(s) that should ultimately be dispensed into the cup. The Executive maintains a record, moreover, of exactly which medication(s) and quantity(s) are presently in the cup. (At the beginning of a run, of course, there are no medications in any cup.) For each cup, and for each medication needed by that cup, the difference between the number that should ultimately be dispensed into the cup and the number of units presently in the cup is referred to as the "number-needed."

Each time the Conveyor advances a step, the Executive updates its record, for each cup, of the position at which that cup is located on the Conveyor. Then, for each cup, the Executive checks (for each drug of that cup for which the number-needed is greater than zero) whether the cup is positioned underneath a drug tube containing a needed drug. If so, the Executive sends a command to the valve pair's active valve to dispense the lesser of the number-needed and the number-remaining in the tube. This is the "number-requested." When the valve finishes such dispensing, it notifies the Executive of the precise number of units that were dispensed (the "number-dispensed"). The Executive then decrements the number-needed of that medication for that cup, by the number-dispensed. Ordinarily, the number-dispensed and the number-requested by the Executive are equal. If the valve malfunctions in the middle of dispensing, however, the number-dispensed may be less than the number-requested. If that happens, or the number-requested was less than the number-needed to begin with (because the number-remaining in the tube prior to dispensing was less than the number-needed), then, after the Executive decrements the number-needed by the number-dispensed, number-needed will still be greater than zero. Therefore, after dispensing takes place, the Executive checks whether the number-needed is still greater than zero. If so, the Executive notes that the active tube needs replacing, re-designates the backup tube as the active tube, and sends it a command to dispense the updated number-needed. Thus, after both tubes have finished dispensing, the cup contains the required number of units of that medication.

If there is one drug that is in particularly high demand, this centralized-control HDDS embodiment provides the hospital, nursing home, or other institution, with the option to configure the Dispensing subsystem so that there are multiple VUs, or more than two ITVs, with the highly demanded medication. In this way, if both tubes of one VU (or pair of ITVs) run out of the medication in the middle of filling an order, the number of units still needed for the order is subsequently dispensed by another valve "down the line" in the assembly, without the tubes having to be replaced mid-run. So, for example, if one cup requires three medicinal units of a particular drug, but there are only two left in a particular VU's tubes, those two are dispensed into the cup when the cup arrives underneath that VU. The Executive records the fact that two have been dispensed, but one more is needed (i.e., both tubes are empty but the number-needed is now 1). Several steps down the line, when the same cup arrives under another VU or ITV containing the same medication, the Executive signals the active valve of that VU or ITV to dispense one unit into the cup.

In the centralized-control HDDS, preferably each Module of the Dispensing subsystem includes one barcode reader that, at each step of the Conveyor, reads and decodes the barcode of the cup that arrives at the first position in that Module. This barcode reader is used to check against errors during a run of the system. Unlike in the decentralized-control HDDS, this reader is not coupled to the control electronics of any valve in the Module, but is instead coupled to the Modules's microprocessor. As noted, at each step of the Conveyor, each barcode reader reads and decodes the barcode of the cup (if any) that arrives at the first position in the Module. It reports this information to the Microprocessor of the Module of which it is a part. The Microprocessor forwards the data to the Executive. As previously explained, the Executive keeps track of where each cup is in the system at each step of the Conveyor. Therefore, to check against errors during the run, at each step, when the Executive receives indicia of the identification of each cup arriving at the first position in each Module, the Executive checks that its data structures also indicate that the same cup is at that spot on the Conveyor. If not, the Executive stops the run and produces an error message on the Control Computer's console (FIG. 2, 26).

5. Drug Storage and Replacement

A typical hospital pharmacy stocks over a thousand different kinds of drugs. Managing and storing a reserve stock of each drug is costly and time consuming, especially as each medication has an expiration date and cannot be stored indefinitely. The invented HDDS helps eliminate the need to store a reserve stock for the medications dispensed by the HDDS, as each drug has a backup tube on line and the system has enough units of each medication to last through at least one full day of operation. The Control Computer monitors the status of each tube, and is connected via computer network to a regional drug refilling center where drugs are loaded into the tubes and shipped to hospitals. As discussed above, the Control Computer (or hospital staff) sends to the center orders for replacement tubes throughout the day, as tubes become empty. These orders are filled by the center, which delivers replacement tubes during the night. In this way the hospital replaces all empty tubes at the beginning of each day.

Some hospitals or nursing homes, however, may not be in a position to receive daily replacements of all needed drugs. For example, an institution's remoteness and severe weather may combine to delay the necessary tube deliveries from time to time; or such daily delivery may not be cost-efficient due to an institution's small size. In such cases, to assure an adequate backup stock and facilitate replacement of empty tubes, the institution stores, for each medication, at least one spare tube on site, but "off-line."

Figure 12:
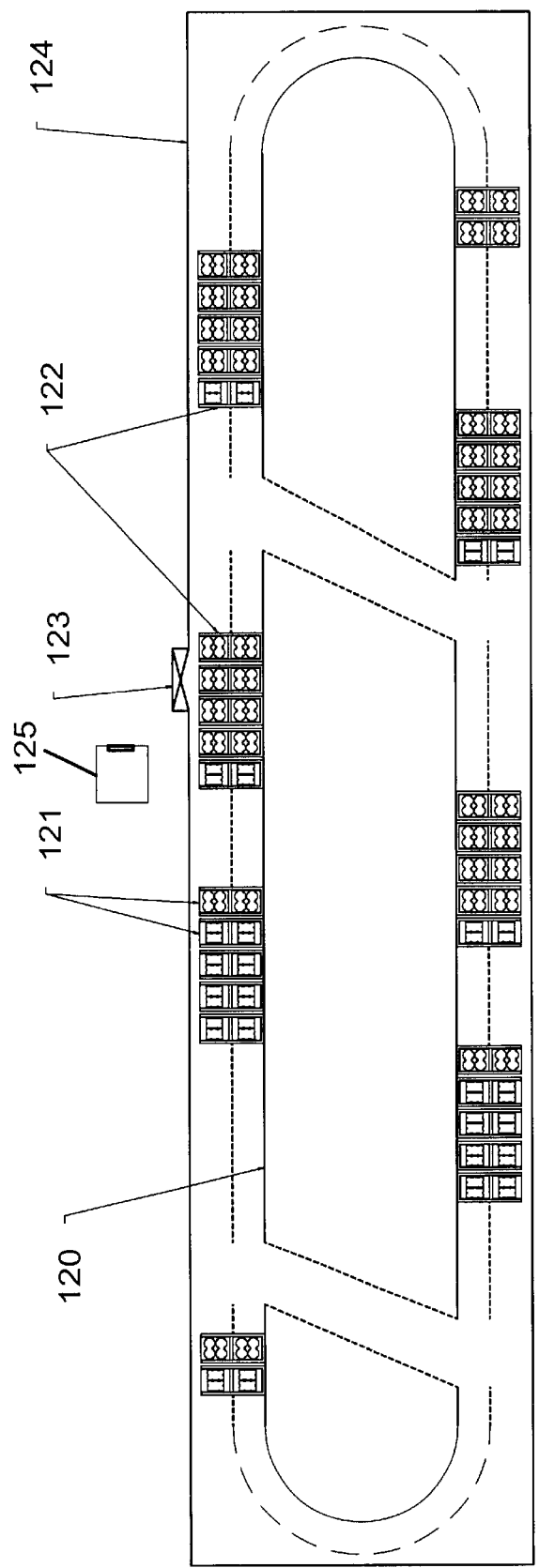
FIG. 12 shows the carousel spare dispenser storage system of the invention.

Such tubes are stored on an oval-shaped Carousel (120), as shown in FIG. 12. Carousel rotation is controlled by a Carousel Control Program running on either the Control Computer or a separate computer linked to the Control Computer. The location of each tube (121) on the Carousel (120) is in the same order as in the HDDS. The spare tubes of each drug are mounted on a special Rack (122). The width of the Rack (122) is preferably approximately 0.6 inches; thus, the total length of the Carousel for 1,000 tubes is approximately 1000×0.6/2 =300 inches, or 25 feet. The width of the Carousel is preferably approximately one foot.

The Carousel (120) is enclosed (124) in a secure manner, so that nobody can remove or replace drug tubes except at a single point through a latched Extraction Door (123). Moreover, no tube is released from the Carousel unless the Control Computer indicates that a replacement is needed for that drug. To support this security measure, each time a drug tube becomes empty and thus needs replacement, indicia of such is forwarded to the Carousel Control Program. The Carousel Control Program maintains a list of drug tubes currently needing replacement in the main HDDS system. This list is sorted according to location of the tubes in the HDDS. When it is time to replace the empty tubes, the attendant submits a password to the Carousel Control Program, which then displays the list of drugs to be replaced, and causes the Carousel to bring the first tube on the list to the Extraction Door. The attendant then scans the code (FIG. 11A. 135) on the replacement tube with reader 125. If it matches the code of the current drug on the list of drugs to be replaced, the latch is released and the attendant removes the tube through the door. Once the tube is removed, the door must be shut before the Carousel will rotate any further. The attendant, therefore, closes the door and places the tube within a Container on a special Cart. Once the tube is in the Container, it can only be accessed through a latched Access Door on the Container.

While the attendant is placing the tube within the Container, after the Extraction Door has shut, the Carousel Control Program causes the Carousel to rotate so as to bring the second tube on the replacement list to the Extraction Door. This process continues until all the tubes on the list have been placed within the Container on the Cart. The carousel preferably rotates in both directions, and the Carousel Control Program determines at the outset in which direction it should rotate to most quickly bring all replacement tubes in the replacement list to the Extraction Door. If it determines that the list should be serviced bottom-up, the Carousel Control Program reverses the order of the list prior to displaying it. In either case, the Carousel Control Program rotates the Carousel in the appropriate direction to replace the tubes in the list's order. This minimizes the time it takes to retrieve all tubes on the replacement list. Once the last tube on the list is released from the Extraction Door and placed on the Cart, the Carousel Control Program deletes the replacement list and starts again from a null list.

To aid the attendant in locating, at the HDDS, the empty tubes that must be replaced, an Indicator Light (95) is turned on at each empty tube when the tube empties out. Such light remains on until the tube is replaced. Additionally, the replacement tubes on the cart are arranged in an order that matches that of the HDDS. When the attendant arrives at an empty tube, he or she scans the barcode on the empty tube and the barcode on the replacement tube. If the drug codes correspond, the Cart's Access Door is released and the attendant removes the tube from the cart and replaces the empty tube.

Loading the Carousel with new tubes is accomplished in a similar manner. The Carousel Control Program is placed into "re-fill" mode through submission of a password and issuance of an appropriate command by the attendant. The barcode on each new tube to be placed into the Carousel is read and entered into the Carousel Control Program, which then rotates the Carousel and brings the correct Rack to the Extraction Door. The attendant reads the barcode on the rack and the barcode on the replacement tube. If the drug codes correspond, the Extraction Door is released and the attendant places the tube on the Carousel at that spot.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A drug dispensing system comprising:
   a) a conveyor having a path along which containers are moved;
   b) at least one container for drugs having a machine-readable indicia bearing information related to the drugs to be dispensed, the container being mountable upon the conveyor for movement along the path;
   c) a plurality of drug dispensing devices disposed above the path,
   d) at least one detection device mounted adjacent to the path such that the detection devices can read the indicia on the containers;
   e) a control computer operatively coupled to the conveyor, drug dispensing devices and detection device; and
   f) at least one tray, capable of mounting to the conveyor, the tray being capable of holding a plurality of containers, wherein the plurality of trays is held to the conveyor by a connector located substantially at a center of a bottom surface of the tray.

2. The drug-dispensing system of claim 1, in which the indicia comprise an identifier of a patient to which the container is assigned.

3. The drug-dispensing system of claim 1, in which the indicia comprise an identifier of at least one drug to be dispensed into the container.

4. The drug-dispensing system of claim 3, in which the indicia further comprise an indication of the quantity of the at least one drug to be dispensed into the container.

5. The drug-dispensing system of claim 1, in which there are a plurality of detection devices, each being coupled to at least one dispensing device, so that as the container is moved by the conveyor along the path, the indicia is read by each of the detection devices as the container moves adjacent to the detection devices; and
   if the information in the indicia is such that a drug in a dispensing device associated with the detection device is to be dispensed into the container, the drug dispensing device is operated to dispense a quantity of the drug into the container.

6. The drug-dispensing system of claim 1, further comprising a container-removing station, such that a container is removed from the conveyor when the container reaches a selected location on the path.

7. The drug-dispensing system of claim 1, further comprising a container-preparation station, such that a container is placed on the conveying means in single file.

8. The drug-dispensing system of claim 1, further comprising a station for application of the indicia upon the containers.

9. The drug-dispensing system of claim 1 wherein the conveyor is an index-driven chain.

10. The drug-dispensing system of claim 1 wherein the path is substantially 'U' shaped.

11. The drug-dispensing system of claim 1, further comprising a container-preparation device which places trays on the conveyor, places containers onto the trays, and affixes labels to the containers.

12. The drug-dispensing system of claim 1, in which each of the drug dispensing devices comprises:
   a tube for storing internally a plurality of solid units of a drug,
   a dispensing valve, connected to the tube, for dispensing one or more of the solid units into a container on the path.

13. The drug-dispensing claim 12, in which the drug dispensing devices further comprise machine-readable indicia identifying a drug stored inside the tube.

14. The drug-dispensing system of claim 12 in which each drug dispensing device further comprises an empty-tube indicator which is activated when the drug tube runs out of units, and the dispensing valve ceases being activated until the empty tube is replaced with a tube containing units.

15. The drug-dispensing system of claim 14 wherein the empty-tube indicator is a light.

16. The drug-dispensing system of claim 12 wherein each drug dispensing device further comprises a special indicator and a manual-mode dispensing member and
   the special indicator is activated in response to a special order for a drug contained in the tube;
   the drug device with an activated special indicator responds to actuation of the manual-mode dispensing member, by dispensing the quantity of the drug stored in its tube required by the special order; and
   the special indicator ceases being activated after the drug-dispensing device dispenses drugs in response to actuation of its manual-mode dispensing member.

17. The drug-dispensing system of claim 16 wherein the special indicator is a light.

18. The drug-dispensing system of claim 16 wherein the manual-mode dispensing member is a switch.

19. The drug-dispensing system of claim 1 in which each drug dispensing device comprises two tubes in adjacent positions, the two tubes comprising a first tube and a second tube, wherein the dispensing device dispenses medications from the first tube, and when first tube cannot dispense a needed medication, the dispensing device dispenses medications from the second tube.

20. The drug-dispensing system claim 19 wherein each of the two tubes is operatively connected to a separate valve, and the drug dispensing device further comprises control electronics operatively connected to the separate valves of the two tubes.

21. The drug-dispensing system of claim 12, further comprising a storage system for additional tubes containing a backup store of drugs, comprising an enclosed powered storage rack for tubes, having an extraction door, such that access to the tubes is only through the extraction door, the tubes being movable along a path to a position adjacent to the extraction door.

22. The drug-dispensing system of claim 21, in which the path is a continuous loop.

23. The drug-dispensing system of claim 21, in which the tubes have machine-readable indicia identifying a drug stored inside the tube, and the storage system further comprises a reader for the machine-readable indicia on the tube.

24. The drug-dispensing system of claim 23, further comprising a control coupled to the powered rack, the extraction door and the reader, such that when a desired drug is requested through the control a tube is moved adjacent to the extraction door, and the extraction door may not be opened until the machine-readable indicia on the tube is read by the reader and the control confirms that the drug identified by the machine-readable indicia matches the desired drug.

* * * * *